US005998594A

United States Patent [19]
Goodman et al.

[11] Patent Number: 5,998,594
[45] Date of Patent: Dec. 7, 1999

[54] SELF-ASSEMBLING, CHROMOGENIC RECEPTORS FOR THE RECOGNITION OF MEDICALLY IMPORTANT SUBSTRATES AND THEIR METHOD OF USE

[75] Inventors: M. Scott Goodman; Andrew D. Hamilton, both of Pittsburgh, Pa.

[73] Assignee: University of Pittsburgh of the Commonwealth System of Higher Education, Pittsburgh, Pa.

[21] Appl. No.: 08/368,209

[22] Filed: Dec. 30, 1994

[51] Int. Cl.$^6$ .......................... C07G 3/00; C07D 213/00; C07D 471/04

[52] U.S. Cl. ........................ 536/18.5; 536/1.11; 536/4.1; 536/18.6; 546/1; 546/26; 546/42; 546/61; 546/79; 546/80; 546/81; 546/112; 552/500; 562/433; 562/562; 562/573; 568/8

[58] Field of Search .................................. 546/1, 88, 10, 546/26, 42, 61, 79, 80, 81, 112; 536/1.11, 4.1, 18.5, 18.6; 552/500; 562/433, 562, 573; 568/8

[56] References Cited

PUBLICATIONS

Dietrich–Buchecker et al., "Une Nouvelle Famille de Molecules: les Metallo–Catenanes", *Tetrahedron Letters*, vol. 24, No. 46, pp. 5095–5098, 1983.

Chapman et al., "A Remarkable Effect of Solvent Size on the Stability of a Molecular Complex", *J. Am. Chem. Soc.*, vol. 111, No. 8, pp. 3075–3077, 1989.

Blundell et al., "The 3–D Structure of HIV–1 Proteinase and the Design of Antiviral Agents for the Treatment of AIDS", *Trends in Biological Chemistry*, vol. 15, pp. 425–430, Nov. 1990.

Tanaka et al., "Two–Point Hydrogen–Bonding Interaction: A Remarkable Chain–Length Selectivity in the Binding of Dicarboxylic Acids with Resorcinol–Aldehyde Cyclotetramer as a Multidentate Host"; *J. Am. Chem. Soc.*, vol. 112, pp. 2807–2808, 1990.

Garcia–Tellado et al., "Molecular Recognition: A Remarkably Simple Receptor for the Selective Complexation of Dicarboxylic Acids", *J. Am. Chem. Soc.*, vol. 112, No. 20, pp. 7393–7394, 1990.

Zimmerman et al., "Improved Binding of Adenine by a Synthetic Receptor", *J. Org. Chem.*, vol. 55, No. 16, pp. 4789–4791, 1990.

Rebek, Jr. et al., "Molecular Recognition and Biophysical Organic Chemistry", *Acc. Chem. Res.*, vol. 23, No. 12, pp. 399–404, Dec. 1990.

Garcia–Tellado et al., "Chiral Recognition of Tartaric Acid Derivatives by a Synthetic Receptor", *J. Chem. Soc., Chem. Commun.*, pp. 1761–1763, 1991.

Zhang et al., "Dissociative Inhibition of Dimeric Enzymes. Kinetic Characterization of the Inhibition of HIV–1 Protease by its COOH–Terminal Tetrapeptide", *The Journal of Biological Chemistry*, vol. 266, No. 24, pp. 15591–15594, Aug. 1991.

Dugas et al., *Bioorganic Chemistry Frontiers: vol. 2*, Springer–Verlag, Jan. 1991.

Kelly–Rowley et al., "Enolate Complexation in Acetonitrile with a Neutral Polyaza Cleft", *J. Am. Chem. Soc.*, vol. 113, pp. 9687–9688, 1991.

Diederich, *Monographs in Supramolecular Chemistry: No. 2 Cyclophanes*, The Royal Society of Chemistry, 1991.

Murakami et al., "Metal–induced Conversion of a 'Closed' Receptor to an 'Open' Receptor on a p–tert–Butycalix[4]arene Diamide Derivative; Fluorescence Detection of a Molecular Recognition Process", *J. Chem. Soc., Chem. Commun.*, No. 20, pp. 1533–1535, 1993.

Drain et al., "Self–assembly of a Bisporphyrin Supramolecular Cage Induced by Molecular Recognition Between Complementary Hydrogen Bonding Sites", *J. Chem. Soc., Chem. Commun.*, pp. 243–245, 1993.

Inouye et al., "Artificial Allosteric Receptors for Nucleotide Bases and Alkali–Metal Cations", *J. Am. Chem. Soc.*, vol. 115, No. 18, pp. 8091–8095, 1993.

Ziessel et al., "Self–Assembly of a New Class of Tetranuclear Copper(I) and Silver(I) Complexes", *Angew. Chem. Int. Ed. Engl.*, vol. 32, No. 6, pp. 877–880, 1993.

Kramer et al., "Self–recognition in helicate self–assembly: Spontaneous formation of helical metal complexes from mixtures of ligands and metal ions", *Proc. Natl. Acad. Sci. USA*, vol. 90, pp. 5394–5398, Jun. 1993.

Fujimoto et al., "Synthesis of and Amine Recognition with a Cu(II)–bridged Biscalix[4]arene", *Tetrahedron Letters*, vol. 35, No. 18, pp. 2915–2918, 1994.

Deng et al., "Allosteric Interaction of Metal Ions with Saccharides in a Crowned Diboronic Acid", *J. Am. Chem. Soc.*, vol. 116, No. 11, pp. 4567–4572, 1994.

Kramer et al., Angew. Chem. Int. Ed. Engl., vol. 32, No. 5, pp. 703–706 (1993).

Kramer et al., Proc. Natl Acad. Sci, vol. 90, pp. 5394–5398 (1993).

*Primary Examiner*—James O. Wilson
*Attorney, Agent, or Firm*—Diane R. Meyers; Arnold B. Silverman; Eckert Seamans Cherin & Mellott, LLC

[57] ABSTRACT

A chromogenic receptor comprises a self-assembled chromogenic compound having at least one intrinsic binding site. The chromogenic compound is characterized by the property of producing a reversible color change responsive to binding a target substrate to the receptor. The chromogenic compound has a transition metal ion and at least one ligand bound to the transition metal ion. The ligand is selected from the group consisting of substituted phenanthroline, substituted 2,2'-bipyridine and substituted 2,2':6',2"-terpyridine. The transition metal is selected from the group consisting of Cu(I), Cu(II), Ag(I), Ni(II), Fe(II), Fe(III), Ru(II), Co(III), and Os(II). Self-assembly can be effected in the presence of Cu(I) to form receptors for dicarboxylic acids, carbohydrate, amino acids, steroids and pyrophosphates. The receptors are characterized by the formation of a 2:1 complex of the target substrate with the receptor producing a visible color change from orange to red and a measurable change in its luminescence. Methods of using these receptors are also disclosed.

62 Claims, 10 Drawing Sheets

SELF-ASSEMBLING, CHROMOGENIC RECEPTORS FOR THE RECOGNITION OF MEDICALLY IMPORTANT SUBSTRATES AND THEIR METHOD OF USE

BACKGROUND OF THE INVENTION

1. Field of the Invention

This invention relates to a self-assembled chromogenic receptor in which the chromophore is an intrinsic part of the binding site and the optical response is dramatic and reversible. The receptor is based on a phenanthroline derivative and the addition of $Cu[CH_3CN]_4^+BF_4^-$ leads to a remarkable self-assembly of a metal templated receptor containing binding sites for medically important substrates. This invention also relates to a method of employing the chromogenic receptors in delineation of medically important substrates in biological solutions.

2. Background Information

The development of synthetic receptors for neutral molecules has been an area of active research in recent years. These systems include complexes stabilized by hydrophobic interactions (e.g., cyclophanes), #—# stacking (e.g., "molecular tweezers"), and hydrogen bonding. Garcia-Tellado et al., J. Chem. Soc., Chem. Commun. 1991, 1761–1763. The study of these complexes has contributed to an understanding of the relative strengths of the various forces involved in binding and a growing knowledge of the subtle design changes that can be used to effect substrate selectivity, including stereoselectivity. Diederich, *Cyclophanes;* The Royal Society of Chemistry: Cambridge, UK, 1991; Hamilton, A. D. In *Bioorganic Chemistry Frontiers;* H. Dugas, Ed.; Springer-Verlag: Berlin, 1991; Vol. 2; pp. 117–174; Rebek, J. J. *Acc. Chem. Res.* 1990, 23, 399; Zimmerman et al., *J. Org. Chem.* 1990, 55, 4789–4791; Tanaka et al., *J. Am. Chem. Soc.* 1990, 112, 2807–2808; Garcia-Tellado et al., *J. Am. Chem. Soc.* 1990, 112, 7393–7394; Kelly-Rowley et al., *J. Am. Chem. Soc.* 1991, 113, 9687–9688; Chapman et al., *J. Am. Chem. Soc.* 1989, 111, 3075–3077.

The success of these systems largely depends on the skills of the synthetic chemist, who must properly orient the binding groups of the receptor to complement those of the intended substrate. While there have been many notable successes using this approach, an alternative method can be envisioned in which a receptor self-assembles from smaller constituents. This strategy is commonly seen in biological receptors. For example, the dimerization of HIV protease is a prerequisite for its biological activity. Blundell et al., *Trends Biochem. Sci.* 1990, 425–430; Zhang et al., *J. Biol. Chem.* 1991, 266, 15591–15594. Self assembly is defined here as two or more separate molecules coming together through noncovalent interactions to form the active receptor. Self-assembled receptors offer several advantages over traditional receptors. Smaller subunits are easier to synthesize than fully elaborated receptors. In addition, careful control over the self assembly process can potentially lead to a large number of different receptors from just a few subunits. Moreover, self assembly has the potential to provide access to very large and complicated receptors for the recognition of large structures (e.g., protein surfaces and DNA). However, to date there have been only limited reports pertaining to the self assembly of synthetic receptors. Drain et al., *J. Chem. Soc., Chem. Commun.* 1993, 243–245; Fujimoto et al., *Tetrahedron Lett.* 1994, 35, 2915–2918.

Ligand coordination to metals has been used extensively to assemble elaborate structures, including helices (Kramer et al., *Proc. Natl. Acad. Sci.,* 1993, 90, 5394–5398; Ziessel et al., *Angew. Chem. Inc. Ed. Engl.,* 1993, 32, 87), multi-component photochemical devices, and catenanes (Dietrich-Buchecker et al., *Tetrahedron Lett.,* 1983, 24, 5095–5098). In addition, receptors have been constructed in which metal coordination to a metal binding site on the receptor produces an allosteric effect on binding at another site. Deng et al., *J. Am. Chem. Soc.,* 1994, 116, 4567–4572; Inouye et al.,*J. Am. Chem. Soc.,* 1993, 115, 8091–8095; Murakami et al., *J. Chem. Soc., Chem. Commun.,* 1993, 1533–1535. However, the use of coordination sites of a transition metal as a template for the self-assembly of a receptor has not received attention.

Therefore, in spite of the prior art disclosures, there remains a very real and substantial need for a self-assembled chromogenic metal chelate receptor with open coordination sites that can be used for metal ion catalyzed reactions on medically important bound substrates. There also is a need for employing a sensitive probe for determination in biological solutions of medically important substrates such as carbohydrates (glucose), steroids (cholesterol), amino acids (lysine), dicarboxylic acids (glutaric acid), and pyrophosphates (adenosine diphosphate).

SUMMARY OF THE INVENTION

The present invention has met the hereinbefore described need. The self-assembled chromogenic receptor of the present invention provides a receptor and a method to directly determine either visually or by spectroscopy the amount of medically important substrates in biological solutions.

The present invention provides a chromogenic receptor comprising a self-assembled chromogenic compound having at least one intrinsic binding site wherein the chromogenic compound is characterized by the property of producing a reversible color change responsive to binding a target substrate to the receptor. The chromogenic compound has a transition metal ion and at least one ligand bound to the transition metal. The ligand is selected from the group consisting of substituted phenanthroline, substituted 2,2'-bipyridine and substituted 2,2':6',2"-terpyridines. Each ligand has at least one substituent and each substituent is selected from the group consisting of phenylboronic acid, phenylphosphate, phenylphosphonate, acylaminopyridine, urea, thiourea, guanidinium, crown ether and hydrophobic groups selected from the group consisting of 3,5-dinitrophenyl, 3,5-dimethoxyphenyl and diphenylmethyl. The transition metal ion is selected from the group consisting of Cu(I), Cu(II), Ag(I), Ni(II), Fe(II), Fe(III), Ru(II), Co(III), and Os(II).

A dicarboxylic acid chromogenic receptor self-assembles from a ligand containing 2-acylaminopyridine groups in the presence of Cu(I) ions to form a bis(2-acylamino-pyridine) receptor. The preferred chromogenic receptor for dicarboxylic acids is di[2,9-bis[4-[(6-methylpyridin-2-yl)amino] carbonyl]phenyl]-1,10-phenanthroline]copper(I) tetrafluoroborate. The dicarboxylic acid substrate hydrogen bonds to two acylaminopyridine groups on the receptor and, because there are four acylaminopyridine groups on the receptor, forms a 2:1 complex with the di[2,9-bis-[4-[(6-methylpyridin-2-yl)amino)carbonyl]phenyl]-1,10-phenanthroline]copper(I) tetrafluoroborate. The dicarboxylic acid is preferably glutaric acid, glutamic acid, aspartic acid, citric acid, pimelic acid, adipic acid, tartaric acid, 1,3-phenylenediacetic acid, succinic acid and isophthalic acid. The most preferred dicarboxylic acid is glutaric acid. The formation of a 2:1 complex between glutaric acid and the bis(2-aminopyridine) receptor produces a visible color change from pale orange to bright red. The formation of the 2:1 complex between glutaric acid and the receptor produces a measurable change in intensity or a shift in emission of its luminescence. The structure of the 2:1 complex is chiral and generally of a double helix configuration.

A carbohydrate chromogenic receptor self-assembles from a ligand containing either two phenylboronic acid groups, two phenylphosphonate groups or two phenylphosphate groups in the presence of Cu(I) ions. The preferred carbohydrate receptors are a bis(phenylboronic acid) receptor, a bis(phenylphosphonate) receptor and a bis (phenylphosphate) receptor. The most preferred receptor is the bis(phenylboronic acid) receptor, di[2,9-bis[3-[((3-boronophenyl)amino)carbonyl]phenyl]-1,10-phenanthroline copper(I) tetrafluoro-borate. The carbohydrate bonds to either the two phenylboronic acid groups, the two phenylphosphonate groups or the two phenylphosphate groups on the receptor and, because there are four of these groups on the receptor, forms a 2:1 complex with the receptor. The preferred carbohydrates are D-glucose, D-galactose and D-mannose. The most preferred carbohydrate is D-glucose. The formation of a 2:1 complex between D-glucose and the bis(phenylboronic acid) receptor produces a visible color change from pale orange to bright red. The formation of the 2:1 complex also produces a change in the luminescence of the receptor. The structure of the 2:1 complex of D-glucose and the bis(phenylboronic acid) receptor is chiral and generally of a double helix configuration.

An amino acid receptor self-assembles from a ligand containing either two 18-crown-6 ether groups or two 1-aza-18-crown-6 ether groups in the presence of Cu(I) ions to form a bis(crown ether receptor) selected from the group consisting of a bis[18-crown-6 ether] receptor and a bis[1-aza-18-crown-6 ether] receptor. The preferred amino acid receptor is the bis[aza-crown ether] receptor, di[2,9-bis[3-((1-aza- 18-crown-6-1-yl)methyl)phenyl]-1,10-phenanthroline]copper(I) tetrafluoroborate. The amino acid hydrogen bonds to two crown ether groups on the receptor. Because there are four crown ether groups on the receptor, the amino acid forms a 2:1 complex with the receptor. The preferred amino acids are selected from the group consisting of lysine, glutaric acid, glycine, L-dopa and 4-aminobutyric acid. The most preferred amino acid is lysine. The structure of the 2:1 complex of lysine with the bis(aza-crown ether) receptor is chiral and generally of a double helix configuration. The receptor is characterized by the property of being responsive to formation of a 2:1 complex between lysine and the receptor, producing a visible color change from pale orange to bright red upon formation of the complex. The formation of the 2:1 complex also produces a measurable change in the intensity or a shift in emission of the luminescence of the receptor.

A steroid chromogenic receptor self-assembles from a ligand containing either two phenyl groups or two diphenylmethyl groups in the presence of copper(I) ions to form a receptor selected from the group consisting of a bis (phenyl) receptor and a bis(diphenylmethyl) receptor. The steroid interacts with two hydrophobic groups on the receptor. Because there are four hydrophobic groups on the receptor, the steroid forms a 2:1 complex with the receptor. The steroid is selected from the group consisting of cholesterol, testosterone, and estrogen. The most preferred receptor is the bis[diphenylmethyl] receptor, di[2,9-bis[3-(diphenylmethyl)phenyl]-1,10-phenanthroline]copper(I) tetrafluoroborate and the preferred steroid is cholesterol. The receptor is characterized by the property of being responsive to formation of a 2:1 complex between cholesterol and the receptor, producing a visible color change from pale orange to bright red upon formation of the complex. The formation of the 2:1 complex also produces a measurable change in the intensity or a shift in the emission of the luminescence of the receptor. The structure of the 2:1 complex of cholesterol with the hydrophobic receptor is chiral and generally of a double helix configuration.

A pyrophosphate chromogenic receptor self-assembles from a ligand containing either two guanidinium groups, two urea groups or two thiourea groups in the presence of Cu(I) ions to form a receptor selected from the group consisting of a bis(guanidinium) receptor, a bis(urea) receptor, and a bis(thiourea) receptor. The preferred receptor is the bis(guanidinium) receptor, di[2,9-bis[4((guanidino)carbonyl)phenyl]-1,10-phenanthroline]copper(I) tetrafluoroborate. The pyrophosphate hydrogen bonds to either the two guanidinium groups, the two urea groups or the two thiourea groups on the receptor and, because there are four of these groups on the receptor, forms a 2:1 complex with the receptor. The pyrophosphate is selected from the group consisting of adenosine diphosphate and adenosine triphosphate. The preferred pyrophosphate is adenosine diphosphate. The structure of the 2:1 complex of adenosine diphosphate with the bis(guanidinium) receptor is chiral and generally of a double helix configuration. The receptor is characterized by the property of being responsive to the formation of a 2:1 complex between adenosine diphosphate and the receptor, producing a visible color change from orange to red upon formation of the complex. The formation of the 2:1 complex also produces a measurable change in the intensity or a shift in the emission of the luminescence of the receptor.

The invention also comprises a method of employing a chromogenic receptor for direct determination of medically important substrates selected from the group consisting of dicarboxylic acids, amino acids, carbohydrates, steroids and pyrophosphates. The method comprises providing a chromogenic receptor, extracting the substrate from aqueous biological solution, dissolving the substrate in an organic solvent selected from the group consisting of chloroform and dichloromethane which contains the chromogenic receptor and directly determining the amount of substrate by one of either qualitative visual inspection or UV-vis spectroscopy. In preferred embodiments, the method employs glutaric acid as the dicarboxylic acid, D-glucose as the carbohydrate, lysine as the amino acid, cholesterol as the steroid and adenosine diphosphate as the pyrophosphate.

Another method for direct determination of medically important substrates selected from the group consisting of dicarboxylic acids, amino acids, carbohydrates, steroids and pyrophosphates comprises providing a chromogenic receptor, achieving a water soluble modification of the receptor by di-oligoethyleneoxy and mono-oligoethyleneoxy substitution on the 4,7; 4,4' or 4' position of a ligand selected from the group consisting of phenanthroline, 2,2'bipyridine and 2,2':6',2''-terpyridine and directly determining the amount of substrate by one of either qualitative visual inspection or UV-vis spectroscopy. In preferred embodiments, the method employs glutaric acid as the dicarboxylic acid, D-glucose as the carbohydrate, lysine as the amino acid, cholesterol as the steroid and adenosine diphosphate as the pyrophosphate.

Another method employs a chromogenic receptor in fiber optic sensors. The method comprises providing a chromogenic receptor coating the exterior of an optical fiber with a polymer selected from the group consisting of PVC, polypropylene and polyethylene, containing the chromogenic receptor, immersing the fiber into a solution to analyze a substrate selected from the group consisting of dicarboxylic acids, amino acids, carbohydrates, steroids and pyrophosphates, sending light through the fiber and measuring the decrease in intensity of returned light due to a color change of the receptor upon substrate binding. In preferred embodiments, this method employs glutaric acid as the dicarboxylic acid, D-glucose as the carbohydrate, lysine as the amino acid, cholesterol as the steroid and adenosine diphosphate as the pyrophosphate.

Another method of using a chromogenic receptor in fiber optic sensors comprises providing a chromogenic receptor, coating a distal end of an optical fiber with a polymer selected from the group consisting of PVC, polypropylene and polyethylene containing the receptor, collecting light from the far side of the polymer and measuring the light intensity in an optical system. The method employs glutaric acid as the dicarboxylic acid, D-glucose as the carbohydrate, lysine as the amino acid, cholesterol as the steroid and adenosine diphosphate as the pyrophosphate.

It is an object of this invention to develop a synthetic chromogenic receptor that selectively binds substrates with a dramatic color change on binding the target substrate.

It is an object of this invention to develop a synthetic chromogenic receptor whose color change is reversible and, therefore, valuable for multiple use sensors.

It is an object of this invention to develop a synthetic chromogenic receptor for organic analytes that is more stable and has a stronger optical response than chromophorically labelled antibodies.

It is an object of this invention to develop a synthetic chromogenic receptor where the reporter group is close to the substrate binding site for stronger optical response.

It is an object of this invention to develop a chromogenic receptor where the reporter group is an intrinsic part of the binding site and the optical response is dramatic.

It is an object of this invention to develop a chromogenic receptor where the dramatic optical response occurs on complexation of a substrate but is reversible when the substrate is unbound.

It is an object of this invention to develop a chromogenic receptor where a transition metal complex is used as a reporter group.

It is an object of this invention to develop a chromogenic receptor that self-assembles in the presence of a transition metal ion to form a transition metal complex used as the reporter group.

It is an object of this invention to develop a receptor that shows a measurable change in intensity or a shift in emission of its luminescence on binding a substrate.

It is another object of the invention to employ the present chromogenic receptor for direct determination of the amount of medically important dicarboxylic acids, amino acids, carbohydrates, steroids and pyrophosphates.

It is another object of the invention to employ the present chromogenic receptor as a glutaric acid detector in biological solution.

It is another object of the invention to employ the present chromogenic receptor as a glucose detector in biological solutions.

It is another object of this invention to employ the present chromogenic receptor as a lysine detector in biological solutions.

It is another object of this invention to employ the present chromogenic receptor as a cholesterol detector in biological solutions.

It is another object of this invention to employ the present chromogenic receptor as a adenosine diphosphate detector in biological solutions.

It is yet another object of the invention to use the chromogenic receptor of the present invention in fiber optic sensors where chromogenic receptor functionalization of the fiber tip leads to large and easily detectable changes on substrate complexation.

These and other objects of the invention will be more fully understood from the drawings and the following description of the invention and the claims appended hereto.

DESCRIPTION OF THE PREFERRED EMBODIMENT

Figure 1:
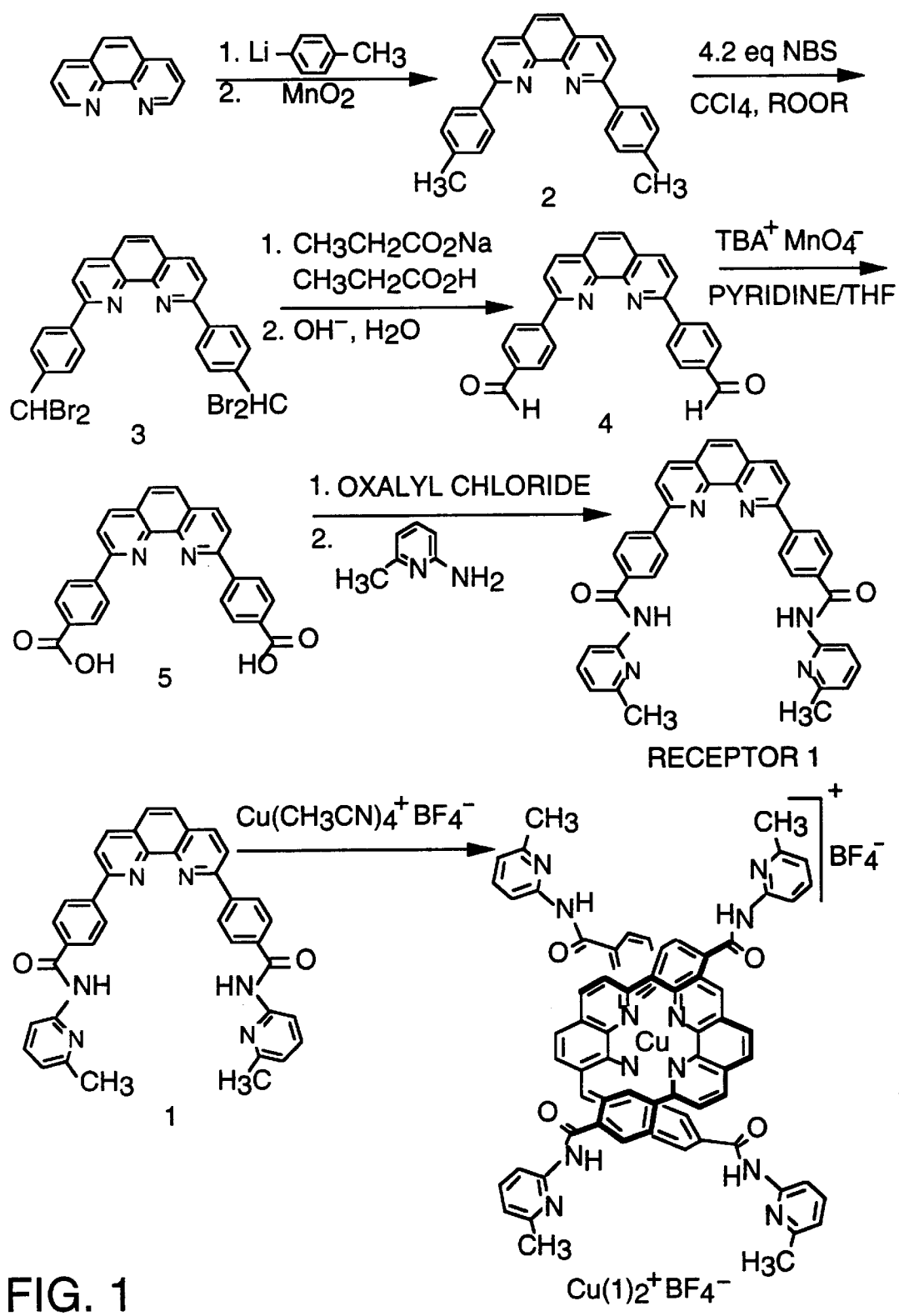
FIG. 1 discloses the synthesis of receptor 1 and the synthesis of $Cu(1)_2^+BF_4^-$.
Figure 2A:
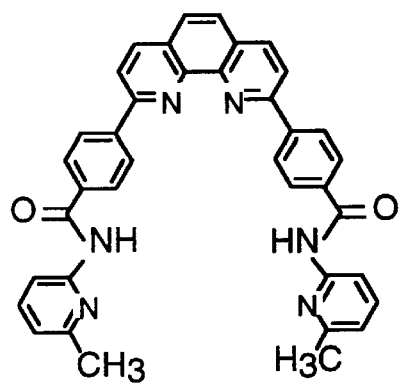
FIG. 2 discloses the structure of receptor 1 and other preferred receptor ligands: dicarboxylic acid receptor ligand 1 (acylaminopyridine groups) (FIG. 2A); pyrophosphate receptor ligand (guanidinium groups) (FIG. 2B); carbohydrate receptor ligand (boronic acid groups) (FIG. 2C); cholesterol receptor ligand (diphenylmethyl groups) (FIG. 2D); and amino acid receptor ligand (1-aza-18-crown-6 groups) (FIG. 2E).
Figure 2B:
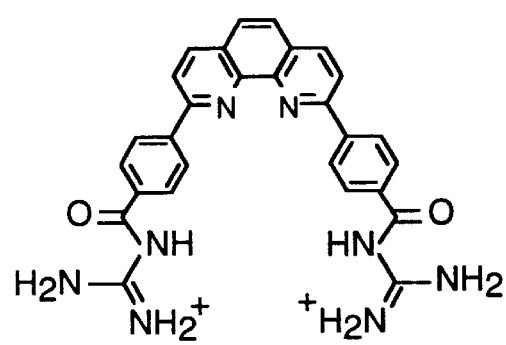
Figure 2C:
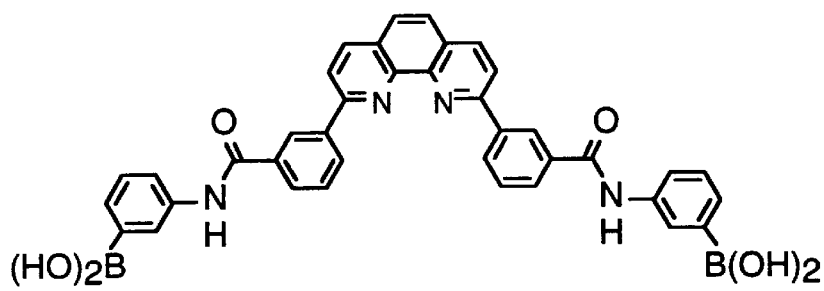
Figure 2D:
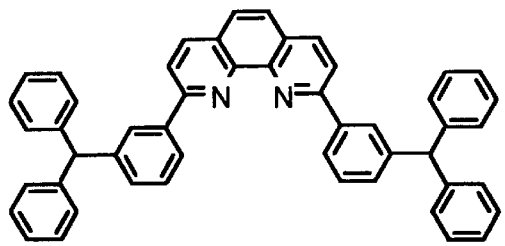
Figure 2E:
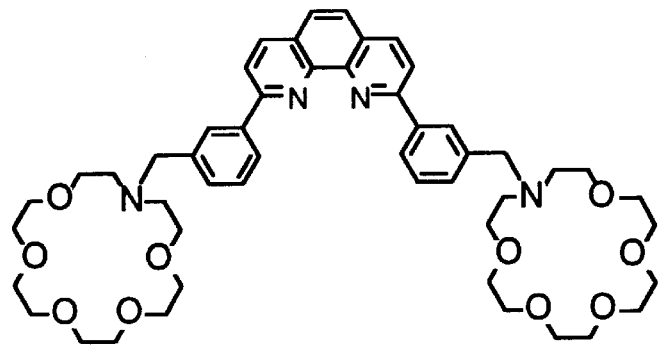

The self-assembled chromogenic receptor of the present invention with a transition metal as a template uses a binding site covalently attached to a ligand. By addition of an appropriate metal ion, chelation brings together two or more binding sites to create the active receptor. This is useful in the creation of biomimetic catalysts wherein a metal chelate receptor can be designed with open coordination spheres for metal ion catalyzed reactions on a bound medically important substrate. The metal chelate is very important because the coordination sphere around a metal can be chiral so the potential for enantioselective binding and reactions exists. Also, the metal complex can be studied by a variety of techniques, such as ESR, NMR, UV-vis spectroscopy and luminescence spectroscopy. The metal ion also provides a sensitive probe for what is occurring in its coordination sphere.

The chromogenic receptor of the present invention provides a method to directly determine either visually or by spectroscopy the amount of medically important substrate in biological solutions.

The present invention provides a chromogenic receptor comprising a self-assembled chromogenic compound having at least one intrinsic binding site where the chromogenic compound is characterized by the property of producing a reversible color change responsive to binding a target substrate to the receptor. The chromogenic compound has a transition metal ion and at least one ligand bound to the transition metal. The ligand is selected from the group consisting of substituted phenanthroline, substituted 2,2'-bipyridine and substituted 2,2':6',2'-terpyridines. The ligand has at least one substituent and each substituent is selected from the group consisting of phenylboronic acid, phenylphosphate, phenylphosphonate, acylaminopyridine, urea, thiourea, guanidinium, crown ether and hydrophobic groups selected from the group consisting of 3,5-dintritrophenyl, 3,5-dimethoxyphenyl and diphenylmethyl. The transition metal ion is selected from the group consisting of Cu(I), Cu(II), Ag(I), Ni(II), Fe(II), Fe(III), Ru(II), Co(III) and Os(II).

The complex formed with the substrates shows up to four hydrogen and other bonds between each substrate and the receptor. The uncomplexed receptor is a pale orange in solution and changes upon complexation with the substrate to a deep red. Complexation also leads to a measurable change in intensity or a shift in emission of its luminescence for the receptor. The color change is reversible when the substrate is unbound. These effects are selective for substrates of a complementary size to bridge the two rigidly held bonding sites.

In one embodiment, a dicarboxylic acid chromogenic receptor self-assembles from a ligand containing two acylaminopyridine groups in the presence of Cu(I) ions to form a bis(2-acylaminopyridine) receptor for dicarboxylic acids. The preferred chromogenic receptor for dicarboxylic acids is di[2,9-bis[4-[(6-methylpyridin-2-yl)amino]carbonyl]phenyl]-1,10-phenanthroline]copper(I) tetrafluoroborate. The dicarboxylic acid substrate hydrogen bonds to two acylaminopyridine groups on the receptor and, because there are four acylaminopyridine groups on the receptor, forms a 2:1 complex with the di[2,9-bis-[4-[(6-methylpyridin-2-yl)amino)carbonyl]phenyl]-1,10-phenanthroline]copper(I) tetrafluoroborate receptor. The dicarboxylic acid is preferably glutaric acid, glutamic acid, aspartic acid, citric acid, pimelic acid, adipic acid, tartaric acid, 1,3-phenylenediacetic acid, succinic acid and isophthalic acid. The most preferred dicarboxylic acid is glutaric acid. The structure of the 2:1 complex is chiral and generally of a double helix configuration.

In another embodiment, a chromogenic receptor for carbohydrates self-assembles from a ligand containing either two phenylboronic acid groups, two phenylphosphonate groups, or two phenylphosphate groups in the presence of Cu(I) ions. The preferred carbohydrate receptors are a bis(phenylboronic acid) receptor, a bis(phenylphosphonate) receptor and a bis(phenylphosphate) receptor. The most preferred receptor is the bis(phenylboronic acid) receptor, di[2,9-bis[3-[((3-boronophenyl)amino)carbonyl]phenyl]-1,10-phenanthroline]copper(I) tetrafluoroborate. The carbohydrate bonds to either the two phenylboronic acid groups, the two phenylphosphonate groups or the two phenylphosphate groups on the receptor and, because there are four of these groups on the receptor, forms a 2:1 complex with said receptor. The preferred carbohydrates are D-glucose, D-galactose and D-mannose. The most preferred carbohydrate is D-glucose. The formation of a 2:1 complex between D-glucose and the bi(phenylboronic acid) receptor produces a visible color change from pale orange to bright red. The structure of the 2:1 complex of D-glucose and the bis (phenylboronic acid) receptor is chiral and generally of a double helix configuration.

In another embodiment, a receptor for amino acids self-assembles from a ligand containing either two 18-crown-6 ether groups or two 1-aza-18-crown-6 ether groups in the presence of Cu(I) ions to form a crown ether receptor selected from the group consisting of a bis[18-crown-6 ether] receptor and a bis(1-aza-18-crown-6 ether) receptor. The preferred amino acid receptor is the bis[aza-crown ether] receptor, di[2,9-bis[3-((1-aza-18-crown-6-1-yl)methyl)phenyl]-10,10-phenanthroline] copper(I) tetrafluoroborate. The amino acid hydrogen bonds to two crown ether groups on the receptor. Because there are four crown ether groups on the receptor, the amino acid forms a 2:1 complex with the receptor. The preferred amino acids are selected from the group consisting of lysine, glutaric acid, glycine, L-dopa and 4-aminobutyric acid. The most preferred amino acid is lysine. The structure of the 2:1 complex of lysine with the bis(crown ether) receptor is chiral and generally of a double helix configuration. The receptor is characterized by the property of being responsive to formation of a 2:1 complex between lysine and the receptor, producing a visible color change from pale orange to bright red upon formation of the complex.

In another embodiment, a chromogenic receptor for steroids self-assembles from a ligand containing either two phenyl groups or two diphenylmethyl groups in the presence of Cu(I) ions to form a receptor selected from the group consisting of a bis(phenyl) receptor and a bis (diphenylmethyl) receptor. The steroid interacts with two hydrophobic groups on the receptor. Because there are four hydrophobic groups on the receptor, the steroid forms a 2:1 complex with the receptor. The steroid is selected from the group consisting of cholesterol, testosterone and estrogen. The preferred receptor is di[2,9-bis[3-(diphenylmethyl)phenyl]-1,10-phenanthroline]copper(I) tetrafluoroborate and the preferred steroid is cholesterol. The receptor is characterized by the property of being responsive to formation of a 2:1 complex between cholesterol and the receptor, producing a visible color change from pale orange to bright red upon formation of the complex. The structure of the 2:1 complex of cholesterol with the hydrophobic receptor is chiral and generally of a double helix configuration.

In yet another embodiment, a chromogenic receptor for pyrophosphates self-assembles from a ligand containing either two guanidinium groups, two urea groups or two thiourea groups in the presence of Cu(I) ions to form a receptor selected from the group consisting of a bis (guanidinium) receptor, a bis(urea) receptor, and a bis (thiourea) receptor. The preferred receptor is the bis (guanidinium) receptor, di[2,9-bis[4-((guanidino)carbonyl)phenyl]-1,10-phenanthroline]copper(I) tetrafluoroborate. The pyrophosphate hydrogen bonds to either the two guanidinium groups, the two urea groups, or the two thiourea groups on the receptor and, because there are four of these groups, forms a 2:1 complex with the receptor. The pyrophosphate is selected from the group consisting of adenosine diphosphate and adenosine triphosphate. The preferred pyrophosphate is adenosine diphosphate. The structure of the 2:1 complex of adenosine diphosphate with the bis (guanidinium) receptor is chiral and generally of a double helix configuration. The receptor is characterized by the property of being responsive to the formation of a 2:1 complex between adenosine diphosphate and the receptor, producing a visible color change from pale orange to bright red upon formation of the complex.

Methods of employing these chromogenic receptors for direct determination of medically important substrates selected from the group consisting of dicarboxylic acids, amino acids, carbohydrates, steroids and pyrophosphates are also presented. One embodiment of this method comprises providing a chromogenic receptor, extracting the substrate from aqueous biological solution, dissolving the substrate in an organic solvent selected from the group consisting of chloroform and dichloromethane containing the chromogenic receptor and directly determining the amount of substrate by one of either qualitative visual inspection or UV-vis spectroscopy. In preferred embodiments, the method employs glutaric acid as the dicarboxylic acid, D-glucose as the carbohydrate, lysine as the amino acid, cholesterol as the steroid and adenosine diphosphate as the pyrophosphate.

Another embodiment of the method for direct determination of medically important substrates selected from the group consisting of dicarboxylic acids, amino acids, carbohydrates, steroids and pyrophosphates comprises providing a chromogenic receptor, achieving a water soluble modification of the receptor by di-oligoethyleneoxy or mono-oligoethyleneoxy substitution on the 4,7; 4,4' or 4' position of a ligand selected from the group consisting of phenanthroline, 2,2'bipyridine and 2,2':6',2"-terpyridine and directly determining the amount of substrate by one of either qualitative visual inspection or UV-vis spectroscopy. In preferred embodiments, the method employs glutaric acid as the dicarboxylic acid, D-glucose as the carbohydrate, lysine as the amino acid, cholesterol as the steroid and adenosine diphosphate as the pyrophosphate.

Another embodiment of the method employs a chromogenic receptor in fiber optic sensors. The method comprises providing a chromogenic receptor coating the exterior of an optical fiber with a polymer selected from the group consisting of PVC, polypropylene and polyethylene, containing the chromogenic receptor, immersing the fiber into a solution to analyze a substrate selected from the group consisting of dicarboxylic acids, amino acids, carbohydrates, steroids and pyrophosphates, sending light through the fiber and measuring the decrease in intensity of returned light due to a color change of the receptor upon substrate binding. In preferred embodiments, this method employs glutaric acid as the dicarboxylic acid, D-glucose as the carbohydrate, lysine as the amino acid, cholesterol as the steroid and adenosine diphosphate as the pyrophosphate.

The final embodiment of the method uses a chromogenic receptor in fiber optic sensors and comprises providing a chromogenic receptor, coating a distal end of an optical fiber with a polymer selected from the group consisting of PVC, polypropylene, and polyethylene, containing the receptor, collecting light from the far side of the polymer and measuring the light intensity in an optical system. In preferred embodiments, the method employs glutaric acid as the dicarboxylic acid, D-glucose as the carbohydrate, lysine as the amino acid, cholesterol as the steroid and adenosine diphosphate as the pyrophosphate.

The synthesis of the dicarboxylic acid receptor (1) shown in FIG. 1 is as follows:

Example I 2,9-bis(4methylphenyl)-1,10-phenanthroline (2). A 1.7 M solution of t-butyllithium in pentane (300 mL, 0.510 mol) was added under argon to a stirred suspension of p-iodotoluene (56.04 g, 0.257 mol) in ether (150 mL) at −78° C. The mixture was allowed to warm to room temperature over 1 h. The resulting solution of tolyllithium was added to a solution of 1,10-phenanthroline monohydrate (8.50 g, 0.043 mol) in toluene (100 mL). The resulting dark red solution was stirred under argon for 48 h. The reaction was carefully quenched with water (300 mL) and extracted with $CH_2Cl_2$ (3×150 mL). The combined organic layers were dried ($Na_2SO_4$) and evaporated to a volume of 500 mL under reduced pressure. The solution of crude product was oxidized by stirring with activated $MnO_2$ (60 g). An additional portion of $MnO_2$ (30 g) was added to the reaction after 1 h to ensure complete oxidation. After a total of 2 h, anhydrous $MgSO_4$ (40 g) was added, and the mixture was filtered. The $MnO_2/MgSO_4$ was washed with $CH_2Cl_2$ (300 mL), and the solvent was concentrated to a volume of 50 mL, when a crystalline solid formed. The solution was cooled in ice and filtered. The light yellow product crystals were filtered, washed with one portion of cold toluene (20 mL), and dried. Yield 8.63 g 56%). $^1H$ NMR ($CDCl_3$) δ8.38 (d, J=8.1 Hz, 4H), 8.29 (d, J=8.5 Hz, 2H), 8.13 (d, J=8.4 Hz, 2H), 7.77 (s, 2H), 7.40 (d, J=8.1 Hz, 4H), 2.47 (s, 6H).

2,9-bis(4-(dibromomethyl)phenyl)-1,10-phenanthroline (3). A mixture of (2) (3.00 g, 8.32 mmol), NBS (6.67 g, 37.5 mmol), and benzoyl peroxide (0.60 g, 2.50 mmol) in $CCl_4$ (6000 mL) was refluxed for 8 h. The reaction mixture was cooled and filtered. The solid obtained was boiled in 1:1 ethanol/water (150 mL) and filtered while hot. The yellow solid was washed with ethanol (50 mL) followed by ether (50 mL). Yield 4.01 g (71%). $^1H$ NMR ($CDCl_3$) δ8.42 (d, J=8.1 Hz, 4H), 8.37 (d, J=8.5 Hz, 2H), 8.15 (d, J=8.4 Hz, 2H), 7.83 (s, 2H), 7.80 (d, J=8.1 Hz, 4H), 6.77 (s, 2H).

2,9-bis(4-formylphenyl)-1,10-phenanthroline (4). Compound (3) (2.00 g, 2.96 mmol) and powdered NaOH (0.71 g, 17.7 mmol) were refluxed in propionic acid (15 mL) for 6 h under argon. The propionic acid was evaporated under reduced pressure and replaced with THF (25 mL) and 2M NaOH (5 mL). The solution was stirred for 1 h, and then the THF was evaporated. Water (20 mL) was added and the pH adjusted to ~8 with HCl. The solution was extracted with $CH_2Cl_2$ (3×100 mL). Yield 0.92 g (80%). $^1H$ NMR ($CDCl_3$) δ8.38 (s, 2H), 8.64 (d, J=8.4 Hz, 4H), 8.42 (d, J=8.4 Hz, 2H), 8.25 (d, J=8.4 Hz, 2H), 8.13 (d, J=8.4 Hz, 4H), 7.89 (s, 2H).

2,9-bis(4carboxylphenyl)-1,10-phenanthroline (5). A solution of $TBA^+MnO_4^-$ (520 mg, 1.44 mmol) in pyridine (10 mL) was added dropwise over 1.5 h to aldehyde (4) (400 mg, 1.03 mmol) dissolved in pyridine (6 mL) and THF (2 mL). The reaction was stirred for an additional 1.5 h. The solution was concentrated to ~4 mL under reduced pressure then poured into a solution of $Na_2SO_3$ (600 mg) in 2N HCl (50 mL). The mixture was stirred 2 h, the precipitate was filtered, and the solid product was rinsed with water (40 mL). The mater was dried in vacuo and used in the next step without further purification. Yield 325 mg (75%). $^1H$ NMR (DMSO-$d_6$) δ8.66 (d, J=8.4 Hz, 4H), 8.64 (d, J=8.4 Hz, 2H), 8.51 (d, J=8.4 Hz, 2H), 8.20 (d, J=8.4 Hz, 4H), 8.06 (s, 2H).

Receptor 1. A suspension of (5) (89 mg, 0.21 mmol) in $CH_2Cl_2$ (6 mL) was treated with oxalyl chloride (110 μL, 1.26 mmol) and a trace of DMF. The mixture was refluxed under argon until all the solid had dissolved (δ6 h). The volatiles were removed under reduced pressure, and the crude acid chloride was dried overnight under vacuum. The acid chloride was suspended in $CH_2Cl_2$ (5 mL) and added to a solution of 2-amino-6-picoline (50 mg, 0.46 mmol) in $CH_2Cl_2$ (2 mL). The resulting homogeneous reaction mixture was stirred for 12 h under a drying tube. The reaction was quenched with sat. $NaHCO_3$ (20 mL) and the organic layer was separated. The aqueous layer was extracted with $CH_2Cl_2$ (2×100 mL), the combined organic layers were dried ($Na_2SO_4$), and evaporated to a yellow foam. The material was purified by flash chromatography (silica gel, 1-5% MeOH/$CH_2Cl_2$), followed by trituration with ethanol (3×20 mL). Yield 70 mg (55%) of light yellow solid. $^1H$ NMR ($CDCl_3$) δ8.75 (br s, 2H), 8.61 (d, J=8.3 Hz, 4H), 8.39 (d, J=8.4 Hz, 2H), 8.26 (d, J=7.8 Hz, 2H), 8.23 (d, J=8.4 Hz, 2H), 8.20 (d, J=8.4 Hz, 4ll), 7.86 (s, 211), 7.69 (t, J=7.8 Hz, 2H), 6.96 (d, J=7.4 Hz, 2H), 2.51 (s, 6H); $^{13}C$ NMR 165.2, 156.7, 155.5, 150.8, 146.2, 142.9, 139.1, 137.2, 134.8, 128.4, 127.9, 127.8, 126.6, 120.4, 119.5, 111.1, 23.9; EIMS m/z (relative intensity) 600 (1, $M^+$), 99(100); FABMS m/z (relative intensity) 601 (100, $MH^+$).

$Cu(1)_2^+BF_4^-$. Receptor 1 (70 mg, 0.12 mmol) was dissolved in $CH_2Cl_2$ (10 mL) and $CH_3OH$ (4 drops) under argon. A solution of $Cu(CH_3CN)_4^+BF_4^-$ (19 mg, 0.060 mmol) in $CH_3CN$ (5 mL) was added and stirred for 1 h. The solvents were evaporated and the resulting red compound was purified by chromatography (silica gel, 5% $CH_3OH$/$CH_2Cl_2$). Yield 75 mg (92%). $^1H$ NMR ($CDCl_3$) δ8.67 (d, J=8.3 Hz, 2H), 8.45 (br s, 2H), 8.10 (d, J=8.2 Hz, 2H), 8.07 (d, J=8.4 Hz, 2H), 7.93 (s, 2H), 7.68 (t, J=7.9 Hz, 2H), 7.55 (d, J=8.1 Hz, 4H), 7.22 (d, J=8.1 Hz, 4H), 6.99 (d, J=7.4 Hz, 2H), 2.55 (s, 6H).

As shown in FIG. 1, dialdehyde 4 was prepared from 1,10-phenanthroline. Compound 4 was carefully oxidized with $TBA^+MnO_4^-$ to the diacid 5. Diacid 5 was converted to the corresponding acid chloride with oxalyl chloride. Treatment of the acid chloride with two equivalents of 2-amino-6-picoline afforded the desired bis(acylaminopyridine) receptor 1.

Receptor 1 was converted as seen in FIG. 1 to the dark red, air stable Cu(I) complex by treatment with 0.5 equivalents of Cu[CH$_3$CN]$_4^+$BF$_4^-$ in CH$_3$CN/CH$_2$Cl$_2$ which was easily purified by chromatography.

Example II

Complexation of Receptor 1 with Dicarboxylic Acids. Receptor 1 is a bis(acylaminopyridine) receptor and as such was expected to form strong bidentate interactions with dicarboxylic acids in chloroform. This was indeed the case, as 1 was found by NMR to bind glutaric acid with an association constant of 3.6×10$^4$ M$^{-1}$. Large changes in proton chemical shifts of 1 indicate that the dicarboxylic acid is hydrogen bonded simultaneously to the two acylaminopyridines moieties. Relatively large shifts were observed in the H3 of the aminopyridine ring (Δδ~0.13 ppm), the amide protons (Δδ~2.4 ppm), and H3, H3' of the phenyl ring (Δδ~0.14 ppm). The contribution of the phenanthroline to binding is uncertain, but it appears to play only a minor role; no protons on the phenanthroline ring shifted more than 0.014 ppm during the course of the titration. The Cu(1)$^+_2$ complex was found to form strong complexes with various dicarboxylic acids in CHCL$_3$. The results are presented in Table 1 below. The stoichiometry of the complexes was 2:1 as determined by the concentration of dicarboxylic acid at which saturation of the receptor was found and independently determined by a Job's plot. A Job's plot is used to measure stoichiometry based on continuous variations of constant concentrations. Binding was most conveniently followed by UV-vis spectroscopy (ΔA$_{550}$) and was checked against NMR results for pimelic acid and glutaric acid. The binding data was analyzed by assuming that two independent and equal bidentate binding sites are interacting with the substrate. In this way a single association constant is obtained that represents the strength of binding of one of the receptor binding sites with one substrate. This method resulted in very good fits to the data in most cases. An exception was N-Cbz-glutamic acid, which is understandable because there are several diastereotopic complexes present (vide infra), each with a different K$_a$.

TABLE 1

UV-vis and NMR Binding Constants for Cu(1)$_2^+$BF$_4^-$ with Dicarboxylic Acids

| Dicarboxylic Acid | Binding Constant (K$_a$) | |
|---|---|---|
| | UV-vis | NMR |
| glutaric acid | 7.8 × 10$^4$ M$^{-1}$ | 7.1 × 10$^4$ M$^{-1}$ |
| pimelic acid | 1.7 × 10$^4$ M$^{-1}$ | 4.0 × 10$^4$ M$^{-1}$ |
| 1,3-phenylenediacetic acid | 3.5 × 10$^4$ M$^{-1}$ | |
| N-Cbz-glutamic acid | 4.0 × 10$^4$ M$^{-1}$ | |

Figure 3:
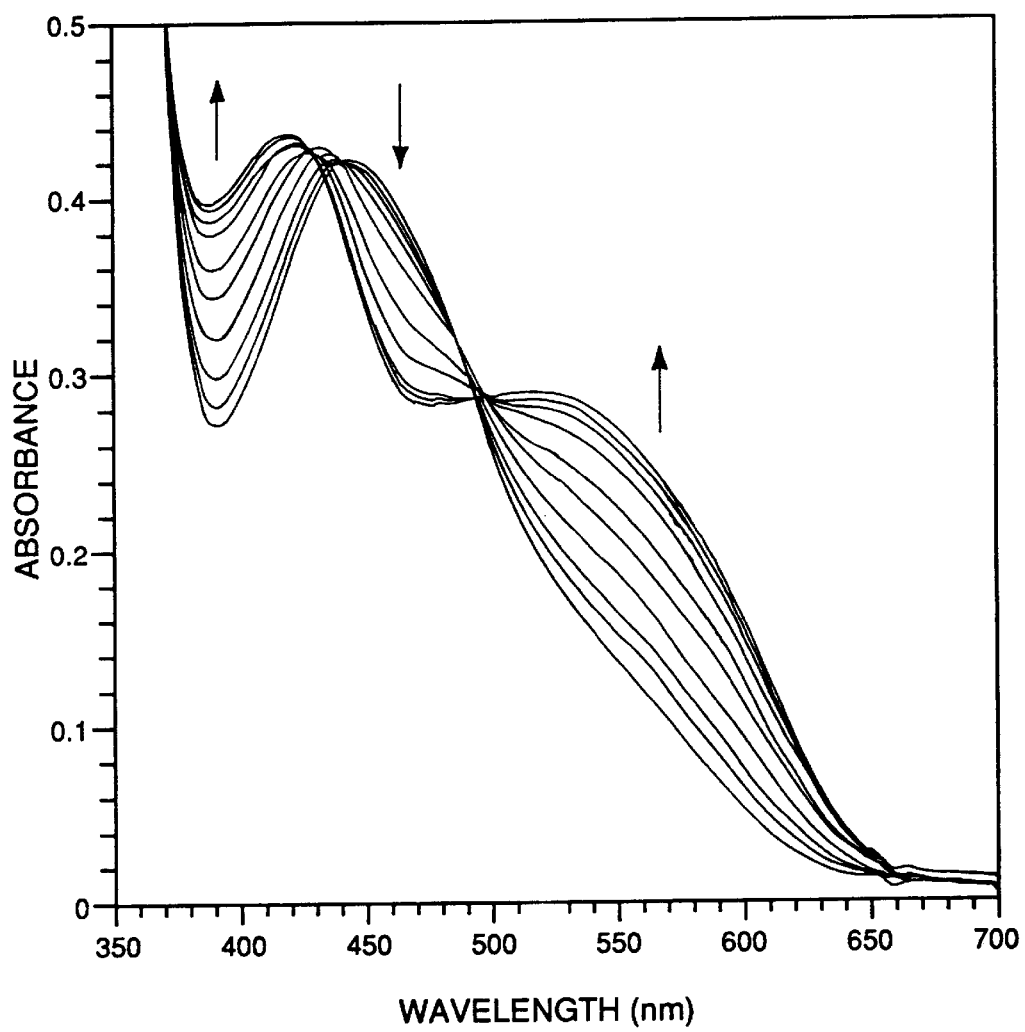
FIG. 3 discloses the change in the visible absorption spectrum of $Cu(1)_2^+BF_4^-$ upon addition of glutaric acid in $CHCl_3$ [$Cu(1)_2^+BF_4^-$]=0.106 mM, [glutaric acid]=0–0.5 mM.
Figure 4:
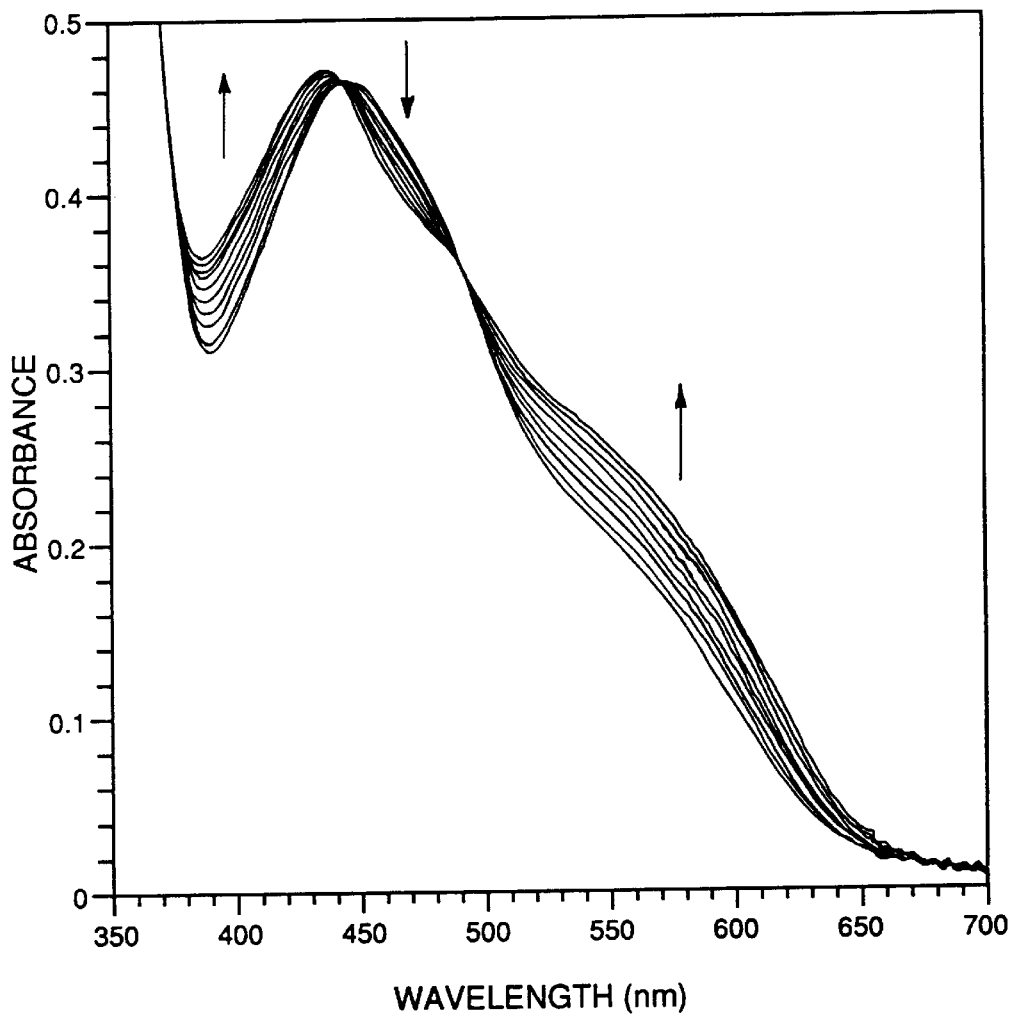
FIG. 4 discloses the change in the visible absorption spectrum of [$Cu(L)_2^+BF_4^-$] upon addition of glutaric acid in $CHCl_3$. [$Cu(L)_2^+BF_4^-$]=0–0.125 mM [glutaric acid]=0–0.40 mM.

In each case above, binding is accompanied by a distinct color change from pale orange to bright red. The change in the visible absorption spectrum of Cu(1)$_2^+$BF$_4^-$ in a typical titration with glutaric acid is shown in FIG. 3. From comparison of FIG. 3 with FIG. 4 which is a change in the visible absorption spectrum of Cu(L)$_2^+$BF$_4^-$ upon addition of glutaric acid, it is clear that the bis-dicarboxylic acid receptor, Cu(1)$_2^+$BF$_4^-$, is more chromogenic than a mono-dicarboxylic acid receptor, Cu(L)$_2^+$BF$_4^-$.

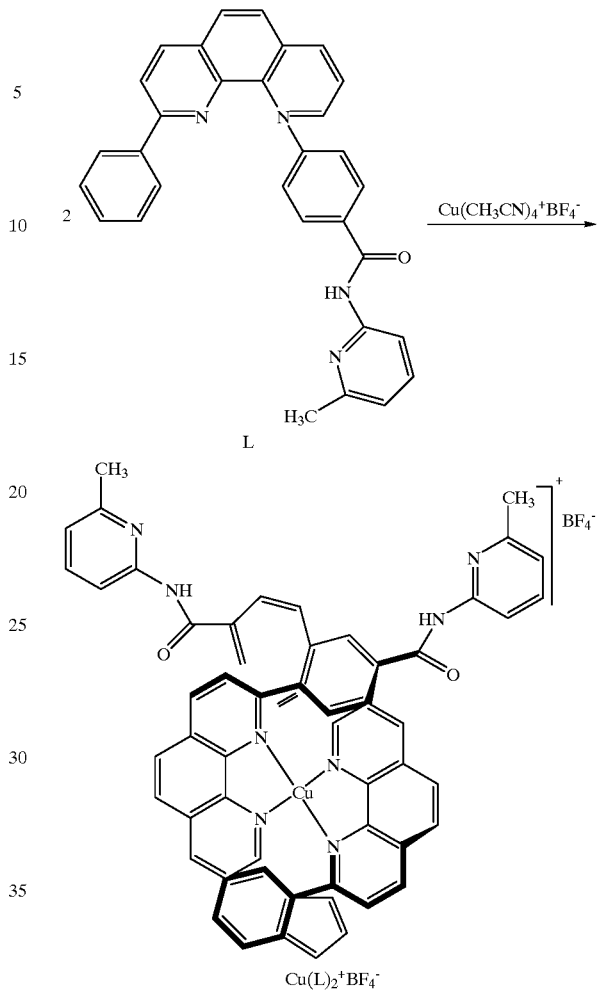

The relative change in A$_{550}$ is 3–4 times greater for Cu(1)$_2^+$BF$_4^-$ than for Cu(L)$_2^+$BF$_4^-$. A summary of the spectral changes that occur upon complex formation are present in Table 2 below. As with Cu(L)$_2^+$BF$_4^-$, there is some variation in the spectrum of the complex that depends on which substrate is being bound. Pimelic acid induced the smallest changes in the spectrum, and 1,3-phenylenediacetic acid caused the largest change.

TABLE 2

UV-vis Spectral Changes of Cu(1)$_2^+$BF$_4^-$ with Dicarboxylic Acids

| Dicarboxylic Acid | λ$_{max}$(nm) 2:1 complex | % Increase (λ = 550 nm) |
|---|---|---|
| glutaric acid | 420, 518 | 101 |
| pimelic acid | 434 | 62 |
| 1,3-phenylenediacetic acid | 422, 534 | 111 |
| N-Cbz-glutamic acid | 420, 526 | 105 |

Also reported in Table 2 are the λ$_{max}$ and the relative change in the absorptivity at 550 nm for each substrate/receptor combination. The changes in the absorption spectra are definitely substrate dependent. For example, complexation of pimelic acid results in a less pronounced increase in the shoulder near the red edge and a smaller blue shift in λ$_{max}$ (for Cu(1)$_2^+$BF$_4^-$,λ$_{max}$=445 nm) than complexation of the 5-carbon acids, glutaric and N-Cbz-glutamic.

Remarkably, a lengthening of the dicarboxylic acid by only two carbon atoms results in half the change in absorptivity upon complexation. The isosbestic points for pimelic acid complexation are also significantly different from those of glutaric acid. This is a reflection of a difference in $\lambda_{max}$ in the two complexes. The sensitivity of the absorption spectrum of the receptor on the substrate is unexpected and is used in the design of chemoselective sensors for other medically important substrates such as carbohydrates, amino acids, steroids, and pyrophosphates.

The results presented here show that the complexation of dicarboxylic acids can be achieved by organizing two "half receptors" around a metal atom. The mono (acylaminopyridine) receptor (L) is a moderate receptor for the dicarboxylic acids, due in part to a second, weaker interaction between one carboxylic acid moiety and the free phenanthroline nitrogens. Coordination of the phenanthroline subunit to Cu(I) affords the fully assembled receptor, which has been shown to bind strongly to several dicarboxylic acids. A similar effect is observed with the analogous receptor 1 except that uncoordinated 1 is a good receptor for dicarboxylic acids due to the presence of two appropriately spaced acylaminopyridines.

Figure 5A:
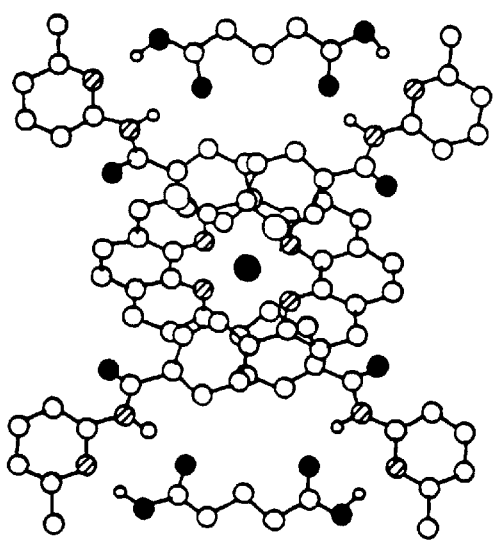
FIG. 5 shows a molecular model of the 2:1 complex formed between glutaric acid and $Cu(1)_2^+BF_4^-$.
Figure 5B:
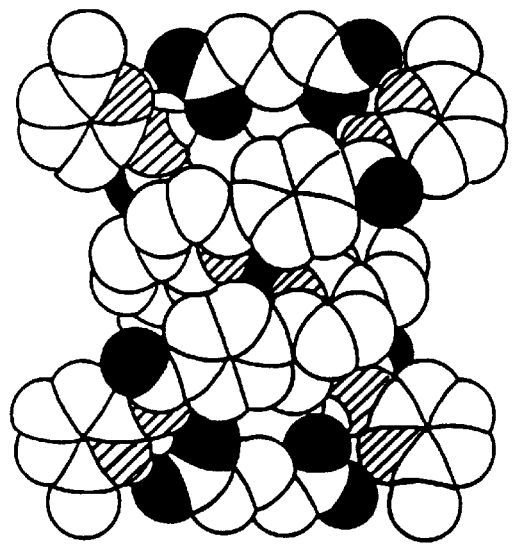
Figure 5C:
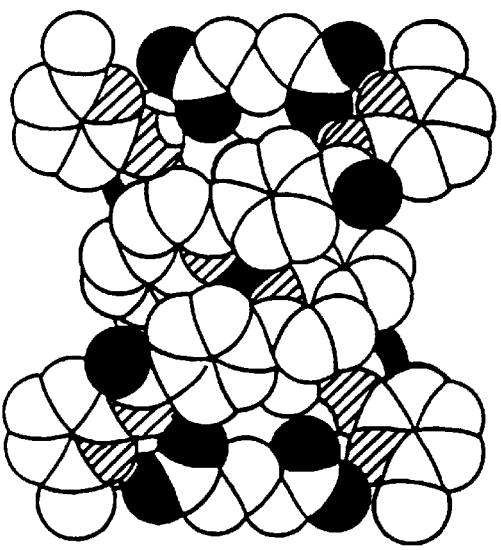

The binding mode for these Cu(I) complexes to dicarboxylic acids was investigated by molecular modeling. Due to limitations in the force fields used, the fully elaborated receptor $Cu(1)_2^+BF_4^-$ could not be energy minimized due to the presence of the metal atom. Instead, the uncoordinated receptor was minimized and manually coordinated to a Cu(I) atom, utilizing bond angles and lengths from X-ray crystal structure of the similar bis(2,9-diphenyl-1,10-phenanthroline)Cu(I) complex. The resulting model is believed to be a useful representation of the structure of the metal complex. The model of the receptor/substrate complex between $Cu(1)_2^+BF_4^-$ and two glutaric acids is shown in FIG. 5. The Cu(I) template allows the formation of a structure whose formation would otherwise be disfavored. The acylaminopyridine binding sites in this structure are nicely oriented for forming strong hydrogen bonds to dicarboxylic acids. If the metal could be removed, after unwinding one would be left with a large macrocyclic 2:2 complex.

In the binding mode proposed in FIG. 5, the structure of the 2:1 complex of glutaric acid with $Cu(1)_2^+BF_4^-$ is chiral, similar to a double helix. It is important to note that the uncomplexed receptor is achiral and becomes chiral only upon complexation of the first dicarboxylic acid. For an achiral substrate this results in a racemic mixture of complexes. For an optically pure dicarboxylic acid such as N-Cbz-glutamic acid, the 2:1 complex is actually a mixture of four different diastereomers. This complicates the analysis of binding because six possibly different binding constants need to be evaluated. For the analysis the assumption was made that all 6 association constants were equal. This resulted in adequate (but not perfect) fits to the data. The alternative of including more variables in the curve fitting routine would necessarily lead to improved fits, but it would not lead to an improved understanding in the present system. The uncomplexed $Cu(L)_2^+BF_4^-$ receptor is chiral, and complexation of an optically pure dicarboxylic acid leads to the formation of two diastereotomeric 1:1 complexes.

Complexes of dicarboxylic acids with Cu(I) templated receptors have significantly different UV-vis spectra than the uncomplexed receptors. The origin of the chromogenic effect is definitely a direct result of the bidentate binding of dicarboxylic acids to the receptors. Addition of large excesses of monocarboxylic acids (acetic or trifluoroacetic) to a $CHCl_3$ solution of either Cu(I)-based receptor leads to only minor changes in the absorbance spectrum. Furthermore, the addition of small amounts of ethanol to the 2:1 glutaric acid/$Cu(l)_2^+BF_4^-$ complex in $CHCl_3$ resulted in a complete reversion to the uncomplexed spectrum.

Figure 6:
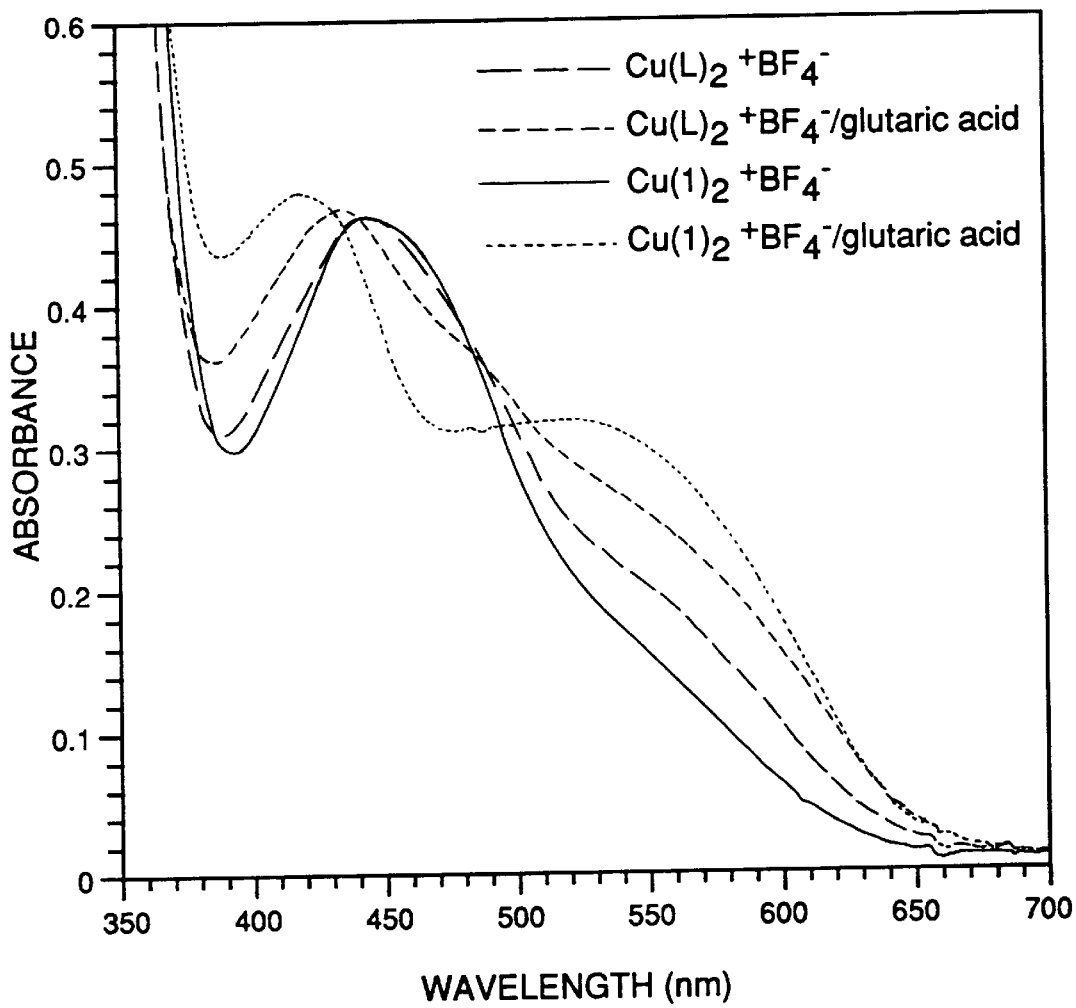
FIG. 6 discloses a comparison of the visible spectrum (in $CHCl_3$) of both Cu(I) based receptors before and after complexation with glutaric acid.
Figure 7:
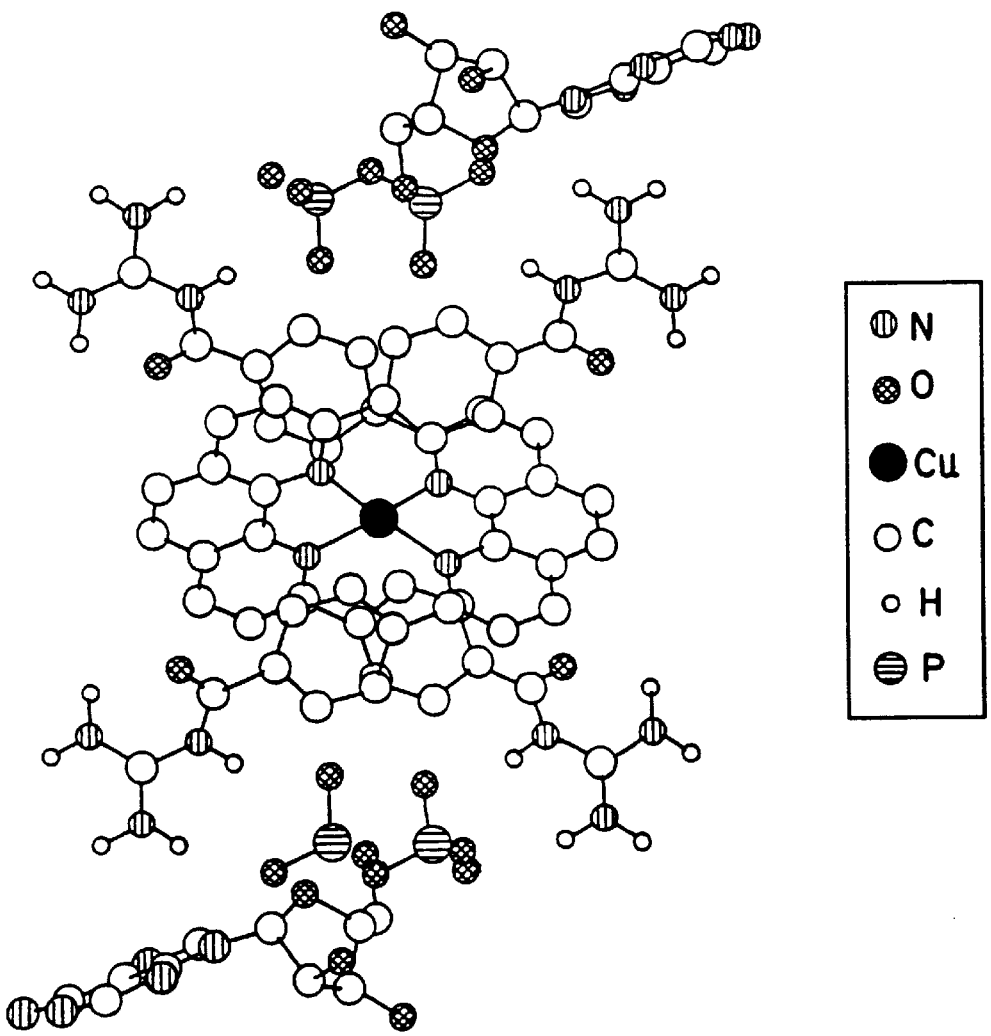
FIG. 7 discloses a molecular model of the 2:1 complex formed between adenosine diphosphate and the Cu(I) guanidinium receptor.
Figure 8:
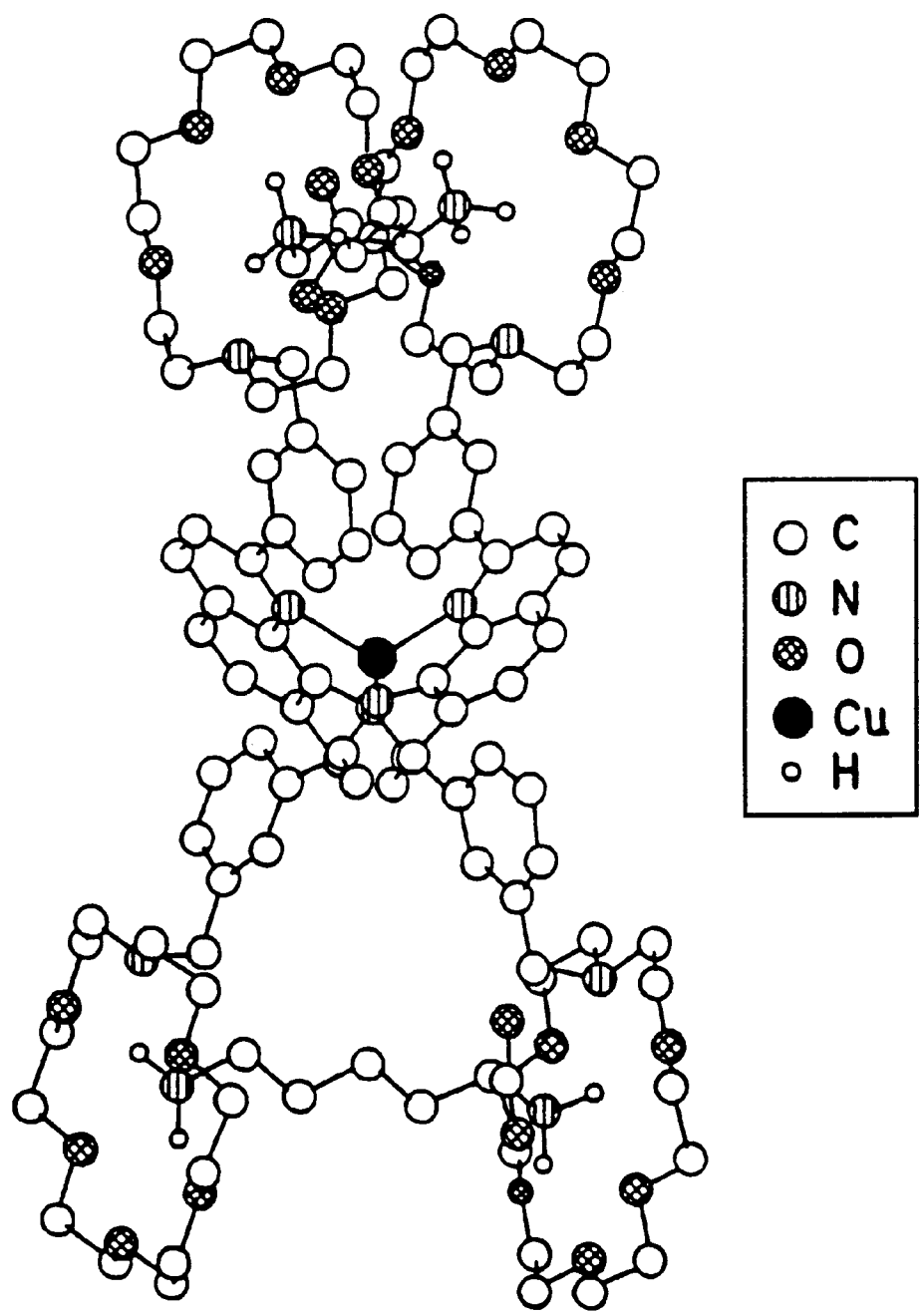
FIG. 8 shows a molecular model of the 2:1 complex formed between lysine and the Cu(I) crown ether receptor.
Figure 9:
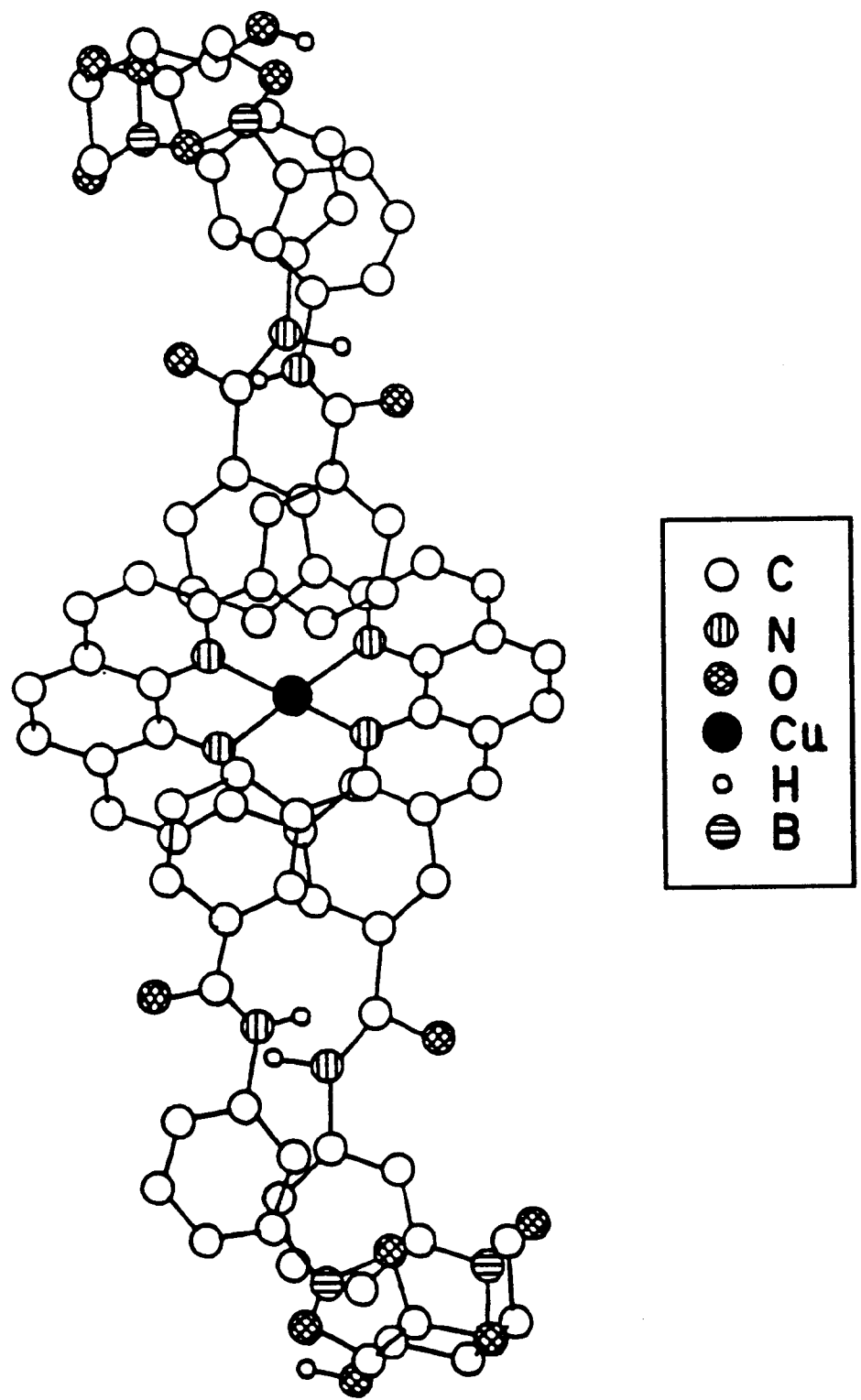
FIG. 9 discloses a molecular model of the 2:1 complex formed between glucose and the Cu(I) boronic acid receptor.
Figure 10:
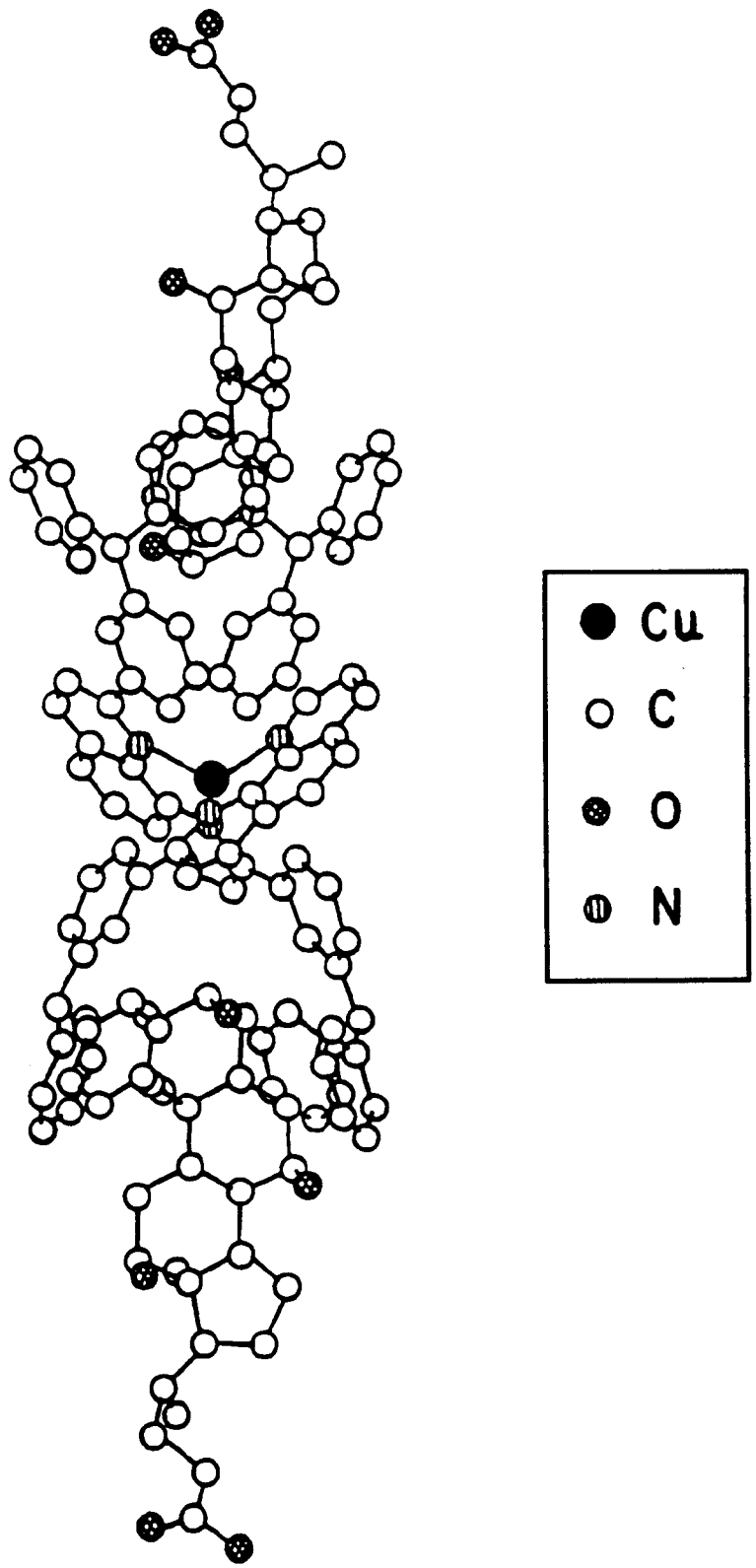
FIG. 10 discloses a molecular model of the 2:1 complex formed between cholesterol and the Cu(I) hydrophobic receptor.

The visible absorbance spectra displayed in FIG. 6 show the chromogenic effect in more detail. It is clear that the shoulder at ~530 nm in the spectra of the Cu(I) templated receptors becomes more pronounced as substrate is added. The shoulder for $Cu(1)_2^+BF_4^-$ is weaker before and more intense after complex formation than the shoulder for $Cu(L)_2^+BF_4^-$. This corresponds to an overall absorbance change in that region that is approximately three times greater for the $Cu(1)_2^+BF_4^-$ complex. This translates into a markedly less color change for the $Cu(L)_2^+BF_4^-$ receptor than for the $Cu(1)_2^+BF_4^-$ receptor upon complexation. Complexation of one equivalent of glutaric acid with $Cu(L)_2^+BF_4^-$ in $CHCl_3$ results in a barely discernible color change from red-orange to orange-red. A similar experiment with two equivalents of glutaric acid and $Cu(1)_2^+BF_4^-$ results in an obvious color change from pale orange to bright red.

The color change upon complexation is unlikely to be caused by simple electronic effects related to the hydrogen bonding interaction. If this were the case, the addition of both monocarboxylic acids and dicarboxylic acids would result in similar color changes in the absorbance spectra of the receptors. A change in the geometry of the receptors is the cause of the observed color changes. Two types of geometrical changes in the receptor can occur upon complexation to accommodate the substrate; one in which the sidearms of the phenanthrolines pinch together decreasing the dihedral angle between the planes of the phenanthrolines and another in which bonds in the sidearms rotate.

Distortion of the pseudotetrahedral coordination sphere around Cu(I) can be discounted based on the following arguments. First, this would not explain the greater color change for the 2:1 dicarboxylic acid/$Cu(1)_2^+BF_4^-$ complex compared to the 1:dicarboxylic acid/$Cu(L)_2^+BF_4^-$ complex as the main distortion should occur during the initial binding event. The complexation of a second dicarboxylic acid to $Cu(1)_2^+BF_4^-$ would produce only minor additional distortion of the coordination sphere. Also, this process should induce positive cooperativity during the binding of the second equivalent of dicarboxylic acid, which is not observed.

Bond rotations in the receptor to properly orient the dicarboxylic acid binding sites are the most likely explanation for the observed chromogenic effect. Among the freely rotating bonds in the sidearms of the receptors, the bond between the phenyl ring and the acylaminopyridine would have the largest influence on the electron density in phenanthroline rings. Such a rotation might reduce the conjugation of the acyl group with the phenyl ring, which in turn would increase the electron density in the phenanthroline. This also explains the substrate dependence of the chromogenic effect. A longer, more flexible substrate such as pimelic acid is able to hydrogen bond with the acylaminopyridines without causing a large conformational change in the receptor. This would lead to a relatively smaller change in the visible absorbance spectrum.

The Cu(I) complexes of (L) and (1) bind dicarboxylic acids with high association constants ($K_a$=0.5–8×104 M$^{-1}$) in $CHCl_3$. The binding was followed by NMR and, more conveniently, by UV-vis spectroscopy. The variation in the absorption spectrum are particularly interesting in that they are large enough to be easily seen as a color change, especially for the complexes of $Cu(1)_2^+BF_4^-$. This chromogenic effect was also surprisingly substrate dependent, with pimelic acid consistently producing the smallest effects. This system serves as a basis for a chemoselective sensor for biologically important dicarboxylic acids (e.g., glutamic acid), amino acids (e.g., lysine), steroids (e.g., cholesterol), pyrophosphates (e.g., adenosine diphosphate), and carbohydrates (e.g., glucose).

The carbohydrate, amino acid, steroid and pyrophosphate receptors can be made as follows:

Example III

[CARBOHYDRATE RECEPTOR] Di-[2,9-bis[3-[((3-boronophenyl)amino)carbonyl]phenyl]-1,10-phenanthroline]copper(I) tetrafluoroborate 2,9-bis(3-methylphenyl)-1,10-phenanthroline can be prepared by reaction of m-tolyllithium (5 equivalents) with 1,10-phenanthroline in toluene followed by $MnO_2$ oxidation. Treatment of 2,9-bis(3-methylphenyl)-1,10-phenanthroline with 4.2 equivalents of NBS in refluxing $CCl_4$ in the presence of peroxides results in the formation of 2,9-bis[3-(dibromomethyl)phenyl]-1,10-phenanthroline. Refluxing the dibromo compound in sodium propionate/propionic acid followed by aqueous hydrolysis with NaOH gives the hydrolyzed product 2,9-bis(3-formylphenyl)-1,10-phenanthroline. Oxidation of the dialdehyde to the dicarboxylic acid can be achieved with 1.33 equivalents $TBS^+MnO_4^-$ in pyridine. The 2,9-bis(3-carboxylphenyl)-1,10-phenanthroline thus obtained can be converted to the diacid chloride with oxalyl chloride and allowed to react with 3-aminophenylboronic acid to give the final ligand. The ligand is mixed with 0.5 equivalents of $Cu(CH_3CN)_4^+BF_4^-$ in $CH_3CN/CH_2Cl_2$ to give the final Cu(I) templated carbohydrate receptor.

[AMINO ACID RECEPTOR] Di[2,9-bis[3-((1-aza-18-crown-6-1-yl)methyl)phenyl]-1,10-phenanthroline]copper (I)tetrafluoroborate 2,9-bis(3-methylphenyl)-1,10-phenanthroline can be brominated with 2.1 equivalents of NBS in refluxing $CCl_4$ in the presence of peroxides. The 2,9-bis[3-(bromomethyl)phenyl]-1,10-phenanthroline thus obtained is allowed to react with 1-aza-18-crown-6 in THF to give the final ligand. The ligand is mixed with 0.5 equivalents of $Cu(CH_3CN)_4^+BF_4^-$ in $CH_3CN/CH_2Cl_2$ to give the final Cu(I) templated amino acid receptor.

[STEROID RECEPTOR] Di[2,9-bis[3-(diphenylmethyl) phenyl]-1,10-phenanthroline]copper(I)tetrafluoroborate 2,9-bis(3-bromophenyl)-1,10-phenanthroline can be prepared by reaction of 5 equivalents of 3-bromo-1-lithiobenzene (prepared from 1,3-dibromobenzene and 1 equivalent of n-butyllithium) with 1, 10-phenanthroline in toluene followed by $MnO_2$ oxidation. Lithiation (n-butyllithium) of the bromo compound followed by treatment with benzophenone produces 2,9-bis[3-hydroxy-1,1-diphenylmethyl)phenyl]-1, 10-phenanthroline, which can be reduced to the final ligand with $NaBH_4$ in trifluoroacetic acid. Coordination of the ligand to 0.5 equivalents of $Cu(CH_3CN)_4^+BF_4^-$ in $CH_3CN/CH_2Cl_2$ gives the final Cu(I) templated hydrophobic steroid receptor.

[PYROPHOSPHATE RECEPTOR] Di[2,9-bis[4-((guanidino) carbonyl)phenyl]-1,10-phenanthroline]copper (I)tetrafluoroborate Compound 5 is treated with 2 equivalents of dicyclohexylcarbodiimide, 4 equivalents of triethylamine, and 2 equivalents of $N^2$, $N^3$-di(t-butoxycarbonyl) guanidine in $CH_2Cl_2$. The resulting Boc-protected guanidine compound can be deprotected with HCl/methanol to give the final ligand. Coordination of the ligand to 0.5 equivalents of $Cu(CH_3CN)_4BF_4^-$ in $CH_3CN/CH_2Cl_2$ gives the final Cu(I) templated pyrophosphate receptor.

Whereas particular embodiments of this invention have been described above for purposes of illustration it will be evident to those skilled in the art that numerous variations of the details of the present invention may be made without departing from the invention as defined in the appended claims.

We claim:

1. A chromogenic receptor comprising a self-assembled chromogenic compound having at least one intrinsic binding site, said chromogenic compound being characterized by the property of producing a reversible color change responsive on binding a target substrate to said receptor.

2. The chromogenic receptor of claim 1, wherein said chromogenic compound has a transition metal ion and at least one ligand bound to said transition metal ion.

3. The chromogenic receptor of claim 2, wherein said ligand is selected from the group consisting of substituted phenanthroline, substituted 2,2'-bipyridine and substituted 2,2':6',2"-terpyridines.

4. The chromogenic receptor of claim 3, wherein said ligand has at least one substituent and each substituent is selected from the group consisting of phenylboronic acid, phenyl phosphate, phenylphosphonate, acylaminopyridine, urea, thiourea, guanidinium, crown ether, and hydrophobic groups selected from the group consisting of 3,5-dinitrophenyl, 3,5-dimethyoxyphenyl and diphenylmethyl.

5. The chromogenic receptor of claim 2, wherein said transition metal ion is selected from the group consisting of Cu(I), Cu(II), Ag(I), Ni(II), Fe(II), Fe(III), Ru(II), Co(III), and Os(II).

6. The chromogenic receptor of claim 4, wherein said substituent is acylaminopyridine and said transition metal is Cu(I) and said receptor is further characterized as a bis(2-acylaminopyridine) receptor for dicarboxylic acids.

7. The chromogenic receptor of claim 6, wherein said chromogenic receptor is di[2,9-bis[4-[[(6-methylpyridin-2-yl)amino]carbonyl]phenyl]-1,10-phenanthroline]copper(I) tetrafluoroborate.

8. The chromogenic receptor of claim 6, wherein said receptor is further characterized by the property of forming a hydrogen bond between two acylaminopyridine groups on said receptor and a dicarboxylic acid.

9. The chromogenic receptor of claim 8, further characterized as forming a complex with said dicarboxylic acid in a 2:1 ratio of said dicarboxylic acid to said receptor.

10. The chromogenic receptor of claim 6, further characterized as complexing with a dicarboxylic acid selected from the group consisting of glutaric acid, glutamic acid, aspartic acid, citric acid, pimelic acid, adipic acid, tartaric acid, 1,3-phenylene diacetic acid, succinic acid and isophthalic acid.

11. The chromogenic receptor of claim 10, wherein said dicarboxylic acid is glutaric acid.

12. The chromogenic receptor of claim 9, wherein the structure of said 2:1 complex of dicarboxylic acid with said receptor is chiral and generally of a double helix configuration.

13. The chromogenic receptor of claim 12, wherein said receptor is further characterized as producing a visible color change from orange to red upon formation of said complex.

14. The chromogenic receptor of claim 13, further characterized by the property of undergoing a change in intensity of its luminescence upon formation of said complex.

15. The chromogenic receptor of claim 4, wherein said substituent is selected from the group consisting of phenylboronic acid, phenylphosphonate and phenylphosphate and said transition metal is Cu(I) and said receptor is further characterized as a carbohydrate receptor selected from the group consisting of a bis(phenylboronic acid) receptor, a bis(phenylphosphonate) receptor, and a bis(phenylphosphate) receptor.

16. The chromogenic receptor of claim 15, wherein said receptor is di[2,9-bis[3-[((3-boronophenyl)amino)carbonyl]phenyl]-1,10-phenanthroline]copper(I) tetrafluoroborate.

17. The chromogenic receptor of claim 15, wherein said receptor is further characterized by the property of forming bonds between either the two phenylboronic acid groups, the two phenylphosphonate groups or the two phenylphosphate groups on said receptor and a carbohydrate.

18. The chromogenic receptor of claim 17, further characterized as forming a complex with said carbohydrate in a 2:1 ratio of said carbohydrate to said receptor.

19. The chromogenic receptor of claim 18, further characterized as complexing with a carbohydrate selected from the group consisting of D-glucose, D-galactose and D-mannose.

20. The chromogenic receptor of claim 19, wherein said carbohydrate is D-glucose.

21. The chromogenic receptor of claim 18, wherein said receptor is further characterized as producing a visible color change from orange to red upon formation of said complex.

22. The chromogenic receptor of claim 18, wherein the structure of said 2:1 complex of carbohydrate and said receptor is chiral and generally of a double helix configuration.

23. The chromogenic receptor of claim 22, further characterized by the property of undergoing a change in intensity of its luminescence upon formation of said complex.

24. The chromogenic receptor of claim 4, wherein said substituent is selected from the group consisting of 18-crown-6 ethers and 1-aza-18-crown-6 ethers and said transition metal is Cu(I) and said receptor is further characterized as an amino acid receptor selected from the group consisting of a bis(18-crown-6 ether) receptor and a bis(1-aza-18-crown-6 ether) receptor.

25. The chromogenic receptor of claim 24, wherein said receptor is di[2,9-bis[3-((1-aza-18-crown-6-yl)methyl)phenyl]-1,10phenanthroline]copper(I) tetrafluoroborate.

26. The chromogenic receptor of claim 24, wherein said receptor is further characterized by the property of forming hydrogen bonds between the two crown ether groups on said receptor and an amino acid.

27. The chromogenic receptor of claim 26, further characterized as forming a complex with said amino acid in a 2:1 ratio of said amino acid to said receptor.

28. The chromogenic receptor of claim 27, further characterized as complexing with an amino acid selected from the group consisting of lysine, glutaric acid, glycine, L-dopa and 4-amino butyric acid.

29. The chromogenic receptor of claim 28, wherein said amino acid is lysine.

30. The chromogenic receptor of claim 27, wherein the structure of said 2:1 complex of amino acid with said receptor is chiral and generally of a double helix configuration.

31. The chromogenic receptor of claim 30, wherein said receptor is further characterized as producing a visible color change from orange to red upon formation of said complex.

32. The chromogenic receptor of claim 31, further characterized by the property of undergoing a change in intensity of its luminescence upon formation of said complex.

33. The chromogenic receptor of claim 4, wherein said substituent is selected from the group consisting of phenyl groups and diphenylmethyl groups and said transition metal is Cu(I) and said receptor is further characterized as a steroid receptor selected from the group consisting of a bis(phenyl) receptor and a bis(diphenylmethyl) receptor.

34. The chromogenic receptor of claim 33, wherein said receptor is di[2,9-bis[3-(diphenylmethyl)phenyl]-1,10-phenanthroline)copper(I)tetrafluoroborate.

35. The chromogenic receptor of claim 33, wherein said receptor is further characterized by the property of undergoing a hydrophobic interaction between either the two phenyl groups or the two diphenylmethyl groups on said receptor and a steroid.

36. The chromogenic receptor of claim 35, further characterized as forming a complex with a steroid in a 2:1 ratio of said steroid to said receptor.

37. The chromogenic receptor of claim 36, further characterized as complexing with a steroid selected from the group consisting of cholesterol, testosterone and estrogen.

38. The chromogenic receptor of claim 37, wherein said steroid is cholesterol.

39. The chromogenic receptor of claim 36, wherein said receptor is further characterized as producing a visible color change from orange to red upon formation of said complex.

40. The chromogenic receptor of claim 39, further characterized by the property of undergoing a change in intensity of its luminescence upon formation of said complex.

41. The chromogenic receptor of claim 36, wherein the structure of said 2:1 complex of said steroid with said hydrophobic receptor is chiral and generally of a double helix configuration.

42. The chromogenic receptor of claim 4, wherein said substituent is selected from the group consisting of guanidinium, urea, and thiourea and said transition metal is Cu(I) and said receptor is further characterized as a pyrophosphate receptor selected from the group consisting of a bis(guanidinium) receptor, a bis(urea) receptor, and a bis(thiourea) receptor.

43. The chromogenic receptor of claim 42, wherein said receptor is further characterized by the property of forming hydrogen bonds between either the two guanidinium groups, the two urea groups or the two thiourea groups on said receptor and a pyrophosphate.

44. The chromogenic receptor of claim 43, wherein said receptor is di[2,9-bis[4-((guanidino)carbonyl)phenyl]1,10-phenanthroline]copper(I) tetrafluoroborate.

45. The chromogenic receptor of claim 43, further characterized as forming a complex with said pyrophosphate in a 2:1 ratio of said pyrophosphate to said receptor.

46. The chromogenic receptor of claim 42, further characterized as complexing with a pyrophosphate selected from the group consisting of adenosine diphosphate and adenosine triphosphate.

47. The chromogenic receptor of claim 46, wherein said pyrophosphate is adenosine diphosphate.

48. The chromogenic receptor of claim 45, wherein the structure of said 2:1 complex of said pyrophosphate with said receptor is chiral and generally of a double helix configuration.

49. The chromogenic receptor of claim 48, wherein said receptor is further characterized as producing a visible color change from orange to red upon formation of said complex.

50. The chromogenic receptor of claim 49, further characterized by the property of undergoing a change in intensity of its luminescence upon formation of said complex.

51. The method of employing a chromogenic receptor for direct determination of medically important substrates selected from the group consisting of dicarboxylic acids, amino acids, carbohydrates, steroids and pyrophosphates, the method comprising:

(a) providing said self-assembled chromogenic receptor;

(b) extracting said substrate from aqueous biological solution;

(c) dissolving said substrate in a organic solvent selected from the group consisting of chloroform and dichloromethane containing said chromogenic receptor; and (d) directly determining the amount of substrate by one of either qualitative visual inspection or UV-vis spectroscopy.

52. The method of claim 51, employing glutaric acid as said dicarboxylic acid.

53. The method of claim 51, employing D-glucose as said carbohydrate.

54. The method of claim 51, employing lysine as said amino acid.

55. The method of claim 51, employing cholesterol as said steroid.

56. The method of claim 51, further employing adenosine diphosphate as said pyrophosphate.

57. The method of employing a chromogenic receptor for direct determination of medically important substrates selected from the group consisting of dicarboxylic acids, amino acids, carbohydrates, steroids and pyrophosphates, the method comprising:

(a) providing said self-assembled chromogenic receptor;

(b) achieving a water soluble modification of said receptor by oligoethyleneoxy substitution on a ligand selected from the group consisting of phenanthroline, 2,2'-bipyridine and substituted 2,2':6',2"-terpyridines; and (c) directly determining the amount of substrate by one of either qualitative visual inspection or UV-vis spectroscopy.

58. The method of claim 57, employing glutaric acid as said dicarboxylic acid.

59. The method of claim 57, employing D-glucose as said carbohydrate.

60. The method of claim 57, employing lysine as said amino acid.

61. The method of claim 57, employing cholesterol as said steroid.

62. The method of claim 57, employing adenosine diphosphate as said pyrophosphate.

* * * * *

UNITED STATES PATENT AND TRADEMARK OFFICE
CERTIFICATE OF CORRECTION

PATENT NO.  :   5,998,594

DATED       :   December 7, 1999

INVENTOR(S) :   Goodman et al.

It is certified that errors appear in the above-identified patent and that said Letters Patent should be corrected as shown below:

Col. 10, line 33 "(86 h)" should read --(~ 6 h)--.

Col. 14, line 61 "($K_2$=0.5-8x104 $M^{-1}$) " should read --($K_a$=0.5-8x$10^4$ $M^{-1}$)--.

Signed and Sealed this

Seventeenth Day of April, 2001

*Attest:*

NICHOLAS P. GODICI

*Attesting Officer*   Acting Director of the United States Patent and Trademark Office